US006552301B2

(12) United States Patent
Herman et al.

(10) Patent No.: US 6,552,301 B2
(45) Date of Patent: Apr. 22, 2003

(54) BURST-ULTRAFAST LASER MACHINING METHOD

(76) Inventors: Peter R. Herman, 589 Bob-o-Link Rd., Mississauga, Ontario (CA), L5J 2P5; Robin Marjoribanks, 148 Macdonell Ave., Toronto, Ontario (CA), M6R 2A6; Anton Oettl, Im Mautnerfeld 1, Weissbach (DE), 83458

( * ) Notice: Subject to any disclaimer, the term of this patent is extended or adjusted under 35 U.S.C. 154(b) by 0 days.

(21) Appl. No.: 09/768,785

(22) Filed: Jan. 25, 2001

(65) Prior Publication Data

US 2001/0009250 A1 Jul. 26, 2001

Related U.S. Application Data
(60) Provisional application No. 60/178,126, filed on Jan. 26, 2000.

(30) Foreign Application Priority Data

Jan. 25, 2000 (CA) .............................................. 2296924

(51) Int. Cl.[7] ........................ B23K 26/00; B23K 26/14; A61B 18/04
(52) U.S. Cl. ............................. 219/121.71; 219/121.7; 219/121.67; 219/121.68; 219/121.69; 606/10; 372/25; 372/53
(58) Field of Search ..................... 219/121.71, 121.7, 219/121.67–121.69; 372/25, 53; 606/10

(56) References Cited

U.S. PATENT DOCUMENTS

| 3,715,596 A | * | 2/1973 | DeMent ...................... 250/253 |
| 3,792,379 A | * | 2/1974 | Auston et al. ............... 359/184 |
| 4,912,696 A | * | 3/1990 | Feyrer et al. ............ 346/135.1 |
| 5,312,396 A | * | 5/1994 | Feld et al. ...................... 606/10 |
| 5,361,275 A | * | 11/1994 | Opower ....................... 372/108 |
| 5,487,080 A | * | 1/1996 | Mukherjee ................... 372/53 |
| 5,624,435 A | * | 4/1997 | Furumoto et al. ............. 606/10 |
| 5,656,186 A | * | 8/1997 | Mourou et al. ......... 219/121.69 |
| 5,720,894 A | * | 2/1998 | Neev et al. ................... 156/345 |
| 6,043,452 A |   | 3/2000 | Besteniehrer |
| 6,050,990 A | * | 4/2000 | Tankovich et al. ............. 606/16 |
| 6,064,682 A | * | 5/2000 | Vickers ........................ 372/25 |
| 6,090,507 A | * | 7/2000 | Grenon et al. ................. 430/5 |
| 6,150,630 A | * | 11/2000 | Perry et al. ............. 219/121.67 |

OTHER PUBLICATIONS

Liu, X. et al., "Laser Ablation and Micromachining with Ultrashort Laser Pulses", Oct. 1997, IEEE Journal of Quantum Electronics, vol. 33, No. 10, pp. 1706–1716.*
Excimer laser ablation of fused silica, J. Ihlemann, Applied Surface Science 54 (1992) 193–200.
Picosecond laser sputtering of sapphire at 266 nm, A.C. Tann et al., Appl. Phys. Lett. 55 (20) Nov. 13, 1989, pp. 2045–2047.

(List continued on next page.)

Primary Examiner—Tom Dunn
Assistant Examiner—L. Edmondson
(74) Attorney, Agent, or Firm—Lynn C. Schumacher; Hill & Schumacher

(57) ABSTRACT

A method of laser processing or laser modification of materials. The combination of ultrafast laser pulses and high-repetition rate (>100 kHz) bursts (or continuous operation) defines a new and unexpected regime for material processing. The high repetition rate controls thermal and/or other relaxation processes evolving between each ultrafast laser pulse that 'prepares' the sample surface or bulk to alter the interaction with subsequent ultrafast laser pulses and thereby improve or optimize the process, or enable a new process, that are not available at lower repetition rate. The addition of this laser-controlled thermal component, and/or the general control of relaxation processes, overcomes several current limitations of ultrafast laser processing at lower repetition rates (<100 kHz), providing means to further harness the many attributes of ultrafast lasers for general material processing and material modification applications.

19 Claims, 15 Drawing Sheets

OTHER PUBLICATIONS

Laser–induced damage in $SiO_2$ and $CaF_2$ with picosecond and femtosecond laser pulses, H. Varel et al., Appl. Phys. A 62, 293–294 (1996).

Femtosecond uv Excimer Laser Ablation, S. Kuper et al., Appl. Phys. B 44, 199–204 (1987).

Writing waveguides in glass with a femtosecond laser, K. M. Davis et al., Optics Letters vol. 21, No. 21, Nov. 1, 1996, pp. 1729–1731.

Laser Ablation and Micromachining with Ultrashort Laser Pulses, X. Liu et al., IEEE Journal of Quantum Electronics, vol. 33, No. 10, Oct. 1997, pp. 1706–1716.

Optical ablation by high–power short–pulse lasers, B. C. Stuart et al., J. Opt. Soc. Am. B., vol. 13, No. 2, Feb. 1996, pp. 459–468.

Pulse–width influence on laser structuring of dielectrics, D. Ashkenasi et al., Nuclear Instruments and Methods in Physics Research B 122 (1997) pp. 359–363.

Micromachining of quartz with ultrashort laser pulses, H. Varel et al., Applied Physics A, A65 pp. 367–373 (1997).

Laser–induced breakdown by impact ionization in $SiO_2$ with pulse widths from 7 ns to 150 fs, D. Du et al., Appl. Phys. Lett. 64 (23) Jun. 6, 1994 pp. 3071–3073.

Precise laser ablation with ultrashort pulses, C. Momma et al., Applied Surface Science 109/110 (1997) 15–19.

Machining of sub–micro holes using a femtosecond laser at 800 nm, P. P. Pronko et al., Optics Communications 114 (1995) 106–110.

\* cited by examiner

BURST-ULTRAFAST LASER MACHINING METHOD

CROSS REFERENCE TO RELATED UNITED STATES PATENT APPLICATIONS

This patent application relates to U.S. Provisional patent application Ser. No. 60/178,126, filed on Jan. 26, 2000, entitled BURST-ULTRAFAST LASER MACHINING METHOD.

FIELD OF THE INVENTION

The present invention relates generally to methods of laser processing and modification of materials, and more particularly the present invention relates to laser processing and modification of a variety of materials using ultrafast laser pulses.

BACKGROUND OF THE INVENTION

Many efforts in the current generation of laser processing of materials can be described as investigating new modalities in which the laser fluence may be delivered to a workpiece, specifically the ways in which the pulse duration, wavelength or pulse-shape give significant new control over the laser-material interaction.

Various studies have shown that laser material processing in the ultrashort-pulse regime (<100 picosecond) offers numerous advantages compared with longer pulses, see for example S A. Kuper and M. Stuke, Appl. Phys. B 44, 2045 (1987); S. Press and M. Stuke, Appl. Phys. Lett 67, 338 (1995); C. Momma et al., Optics Comm., 129, 134 (1996); C. Momma et al., Appl. Surf. Sci., 109/110, 15 (1997); D. von der Linde, K. Sokolowski-Tinten, and J. Bialkowski, *Appl. Surf. Sci.* 109/110, 1 (1997); X. Liu, D. Du, and G. Mourou, *IEEE J. of Quantum Electron.* 33, 1706 (1997) J. X. Zhao, B. Hüttner, and A. Menschig, SPIE Proc Vol. 3618, (1999); U.S. Pat. No. 5,361,275; U.S. Pat. No. 5,656,186; U.S. Pat. No. 5,720,894; U.S. Pat. No. 6,090,507; U.S. Pat. No. 6,150,630; U.S. Pat. No. 6,043,452; and patent publication WO 89/08529. The first reported advantages in ultrafast laser processing by S A. Kuper and M. Stuke, Appl. Phys. B 44, 2045 (1987) and patent publication WO 89/08529 emphasized improvements in surface morphology, absence of thermal degradation, and reduced threshold fluence for polymers and inorganic non-metallics such as teeth when using sub-picosecond ultraviolet lasers in comparison with traditional nanosecond ultraviolet lasers. Ultrashort lasers offer high intensity to micromachine, to modify and to process surfaces cleanly by aggressively driving multi-photon, tunnel ionization, and electron-avalanche processes, see J. Ihlemann, *Appl. Surf. Sci.* 54 (1992) 193; D. Du, X. Liu, G. Korn, J. Squier, and G. Mourou, *Appl. Phys. Lett.* 64 (1994) 3071; P. P. Pronko, S. K. Dutta, J. Squier, J. V. Rudd, D. Du, G. Mourou, *Optics Comm.* 114 (1995) 106; B. C. Stuart, M. D. Feit, S. Herman, A. M. Rubenchick, B. W. Shore, M. D Perry, *J. Opt. Soc. Am B* 13 (1996) 459; and C. B. Schaffer, A. Brodeur, N. Nishimura, and E. Mazur, *SPIE* 3616 (1999) 143.

Beyond the simple delivery of 'raw' fluence, lasers offer the parameters of intensity, wavelength, and pulse duration as factors which afford control over essential aspects of material interaction. Particularly, ultrafast laser interactions have well-defined 'damage' thresholds offering improved precision in processing applications, including the fabrication of hole sizes that are smaller than the beam diameter, see U.S. Pat. No. 5,656,186; X. Liu, D. Du, and G. Mourou, *IEEE J. of Quantum Electron.* 33, 1706 (1997) and D. Du, X. Liu, G. Korn, J. Squier, and G. Mourou, *Appl. Phys. Lett.* 64 3071 (1994). Much recent literature has been devoted to ultrafast laser damage and processing of transparent or wide-bandgap materials, see J. Ihlemann, *Appl. Surf. Sci.* 54 (1992) 193, D. Du, X. Liu, G. Korn, J. Squier, and G. Mourou, *Appl. Phys. Lett.* 64 (1994) 3071. Nonlinear absorption mechanisms are key to coupling laser energy into such non-absorbing media.

The thermal impact of picosecond and femtosecond laser interactions is highly limited, confining laser energy dissipation to small optical penetration depths with minimal collateral damage. This precisely confined laser 'heating' minimizes the energy loss into the underlying bulk material, providing for an efficient and controllable ablation process, see U.S. Pat. No. 5,656,186; U.S. Pat. No. 5,720,894; U.S. Pat. No. 6,150,630; S. Preuss, A. Demchuk, and M. Stuke, Appl. Phys. A, 61, 33 (1995); and T. Götz and M. Stuke, Appl. Phys. A, 64, 539 (1997). Because the laser-matter interaction is so brief, there is a shift in the partition of absorbed energy. Relatively thin layers of near-solid density material are heated, during ultrafast-laser interaction, and this enhances evaporative cooling: though the speed of expansion of the volume of heated material is largely fixed by the temperature, the factor increase in volume of a thin layer is much greater. The volume of tenuous heated material more quickly decouples thermally from the bulk, in the case of ultrafast laser-matter interaction, and in this brief time less heat is transferred from the laser-absorption zone to the underlying bulk material. A greater proportion of absorbed energy is carried away in the evaporated material than is the case for longer-duration pulses.

Collectively, these ultrafast laser effects in small volumes minimize thermal transport, mechanical shocks, cracks, charring, discolouration, and surface melting in the nearby laser interaction zone. Ultrafast laser machining permits repair of ultrafine (sub-mircron) defects on photomasks, see U.S. Pat. No. 6,090,507. Such interactions also reduce pain during medical procedures (see U.S. Pat. No. 5,720,894) and enable the microshaping of explosive materials without deflagration or detonation (see U.S. Pat. No. 6,150,630). The short duration further ensures that, all of the laser energy arrives at the surface before the development of a significant ablation plume and/or plasma; such efficient energy coupling is not available with longer duration (>10's ps) laser pulses because of plasma reflection, plasma and plume scattering, and plume heating. Such ultrafast-processing features are highly attractive for the precise microprocessing of good heat conductors such as metals; at the same time, nonlinear absorption of these intense ultrafast pulses also reduces the ablation threshold for wide-bandgap or "transparent" optical materials such as silica glasses.

Ultrafast lasers also offer the means to internally process transparent glass. Microexplosions provide opportunities for 3-D optical storage (C. B. Schaffer, A. Brodeur, N. Nishimura, and E. Mazur, *SPIE 3616* (1999) 143) while refractive index structures such as volume gratings and waveguides (K. M. Davis, K. Miura, N. Sugimoto, and K. Hirao, *Opt. Lett.* 21 (1996)1729) have been formed, by the permanent alteration of the local index of refraction.

These prior studies and developments of ultrashort-laser processing of materials have centered on ultrafast systems with pulse rates typically operating in the ~1 Hz to 10,000 kHz regime. A high-repetition rate three-pulse laser system is described by Opower in U.S. Pat. No. 5,361,275 with pulse separations of 0.5 to 5 ns (200 to 2000 MHz); each pulse is a different wavelength, delivered such that a subsequent pulse arrives soon enough to still interact with the expanding plume of the previous pulse, thereby to benefit from more uniform heating of the plasma plume.

While ultrafast lasers offer exciting prospects for processing materials, at present undesirable effects exist and processing windows are poorly defined. Effects requiring more control in laser processing and modification of materials includes, for example, incubation (defect generation) effects that change etching rates, self-focusing and clouding effects, 'gentle' and 'strong' ablation phases developing with increasing number of pulses, pre-pulse or pedestal effects, poor morphology,: periodic surface structures, melt, debris, surface swelling, shock-induced microcracking, slow processing rates and saturation of hole depth in via/hole formation.

It is advantageous to provide a method of laser processing of materials that addresses the aforementioned difficulties present in present processing methods.

SUMMARY OF THE INVENTION

The present invention provides a method of processing and/or modifying materials based on high repetition-rate (continuous or pulsetrain-burst) application of ultrafast laser pulses to materials. The high-repetition rate provides a new control over laser interactions by defining the arrival time of subsequent laser pulse(s), for example: to be after the timescale of plasma-plume expansion and dissipation, but before thermal and other relaxation processes in the material have fully evolved. In one embodiment, the present invention provides a novel method of controlling the delivery of laser fluence to a material during laser processing that reduces unwanted damage in the material.

In one aspect of the invention there is provided a method of laser induced modification of a material, comprising:

applying at least one burst of laser pulses to a material, the laser pulses having a time separation between individual laser pulses in a range appropriate so as to exploit the persistence of a pre-selected transient effect arising from the interaction of a previous pulse with the material, said laser pulses having a pulse width of less than about 10 picoseconds, and collectively having fluence above a threshold value for modification of said material.

The invention may also provide a method of laser material processing, comprising providing a material to be processed and applying laser pulses to a target zone on the material, the laser pulses having a time separation between individual laser pulses sufficiently long to permit hydrodynamic expansion of a plume and/or plasma so that a next subsequent laser pulse is not substantially reflected, scattered and/or absorbed by the plume and/or plasma, and the laser pulses having a time separation between laser pulses sufficiently short so that a thermal and/or other relaxation process (for example, mechanical, stresses, melt phases, metastable or long-lived states, transient species, shock waves, discoloration, deformation, absorption spectrum, fluorescence spectrum, chemical structure) in the target zone presents heated material or material alternated from the relaxed state to successive laser pulse(s).

The laser pulses may be applied at rates above 100 kHz, wherein thermal transport does not completely dissipate the heat deposited and/or transported in or near the processing volume by each laser pulse, or wherein other relaxation processes have not fully dissipated in or near the processing volume of each laser pulse. A region of warmed material is therefore preserved, and presented to each subsequent laser pulse.

This thermal component and other relaxing processes offer a new modality for controlling ultrafast-laser processing. By adjusting the pulse-to-pulse separation (inverse of repetition rate), the temperature rise, and the extent of the residually heated zone is controlled. In another embodiment, a subsequent laser pulse can be presented at a critical time in the evolution of material properties in or nearby the laser interaction zone to alter the subsequent laser interactions for a controlled change and/or improvement in the laser process. For material heating, subsequent laser interactions offer several advantages and opportunities that are not available for material processing at lower repetition rate, as for example, when the sample interaction has relaxed to close to the substrate temperature. An increased temperature dramatically alters the materials properties in a manner that can positively affect the ultrafast interaction, and control subsequent events such as shock development, defect formation, annealing, surface morphology, debris formation, plume evolution, material removal rates, and geometry of excisions. The combination of high-repetition rate with ultrafast laser pulses provides added control and new avenues in material processing that have not been described before.

BRIEF DESCRIPTION OF THE DRAWINGS

The following is a description, by way of example only, of the method of laser processing of materials in accordance with the present invention, reference being had to the accompanying drawings, in which:

FIG. 1b shows a depth profile corresponding to the hole shown in FIG. 1a;

FIG. 11b are SEM photographs of the holes of FIG. 11a but taken from the rear surface of the holes with the left (right) hole corresponding to the right (left) hole in FIG. 11a;

DETAILED DESCRIPTION OF THE INVENTION

Prior Art Method of Low Repetition Ultrafast Processing of Glass

Figure 1A:
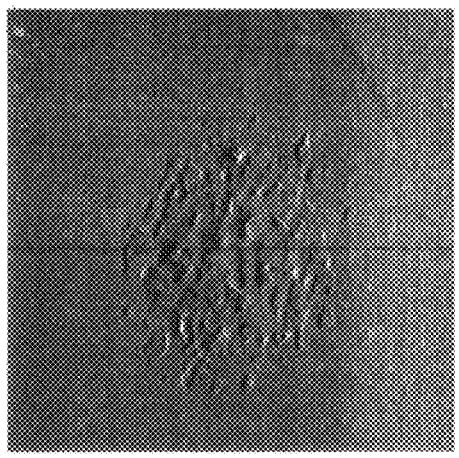
FIG. 1a shows an atomic force microscopy (AFM) image of a micro-hole in fused silica, drilled by a single 1.2 ps laser pulse with a peak fluence of 9.1 J/cm$^2$ using a Prior Art method.
Figure 1B:
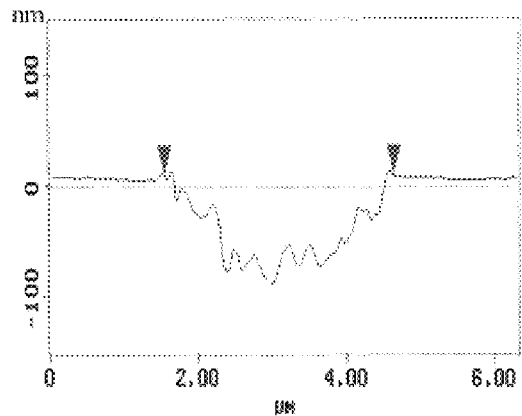
Figure 1C:
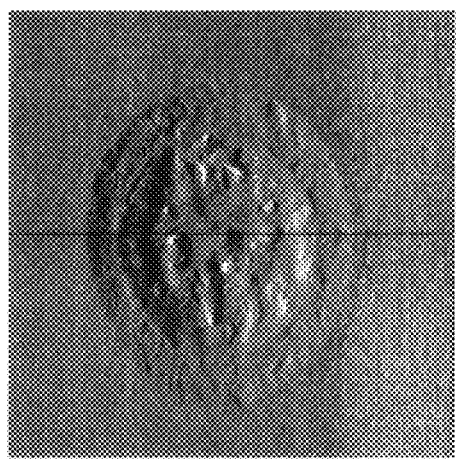
FIG. 1c shows an atomic force microscopy (AFM) image of a micro-hole in fused silica, drilled by a single 1.2 ps laser pulse with a peak fluence of 38 J/cm$^2$ (bottom)
Figure 1D:
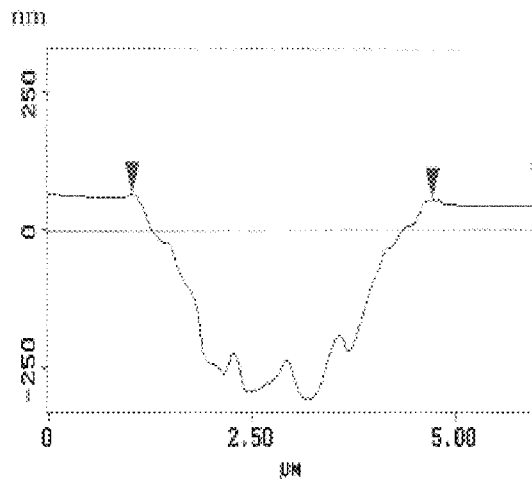
FIG. 1d shows a depth profile corresponding to the hole shown in FIG. 1c.

In this section, results of 1.2-ps laser ablation of fused silica and BK7 at repetition rates of 1 Hz or less are described as a reference to compare with the attributes of burst machining forming the present invention described in the next section. Fused silica and BK7 are highly transparent at the 1.05 µm laser wavelength and yield similar micromachining results. Surface morphology of microholes formed by single laser-pulses are shown in the AFM photographs in FIGS. 1a and 1c. Fluences of 9.1 and 38 J/cm$^2$ each produced moderately smooth holes of ~2.0 µm diameter (FWHM). Surface-profile traces, shown in FIG. 1b (corresponding to FIG. 1a) and FIG. 1d (corresponding to FIG. 1c), reveal hole depths of 100 and 360 nm, respectively.

A small ring structure is observable in the higher-fluence hole, a feature also reported by D. Ashkenasi, H. Varel, A. Rosenfeld, F. Noack, and E. E. B. Campbell, *Nucl. Instr. & Meth. in Phys. Res. B* 122, 359 (1997) for 3.2-ps ablation of fused silica. The excised surface contour was found to crudely follow the laser beam profile, with small-scale surface roughness of ±10% (rms) of the hole depth. This ±10% surface roughness was a general observation for the 'gentle' ablation phase, noted here for fluences, F, less than ~44 J/cm$^2$. Even when several pulses were applied to the same area, surface roughness typically increased in absolute terms, but remained limited to ±10% of the final hole depth.

Figure 2:
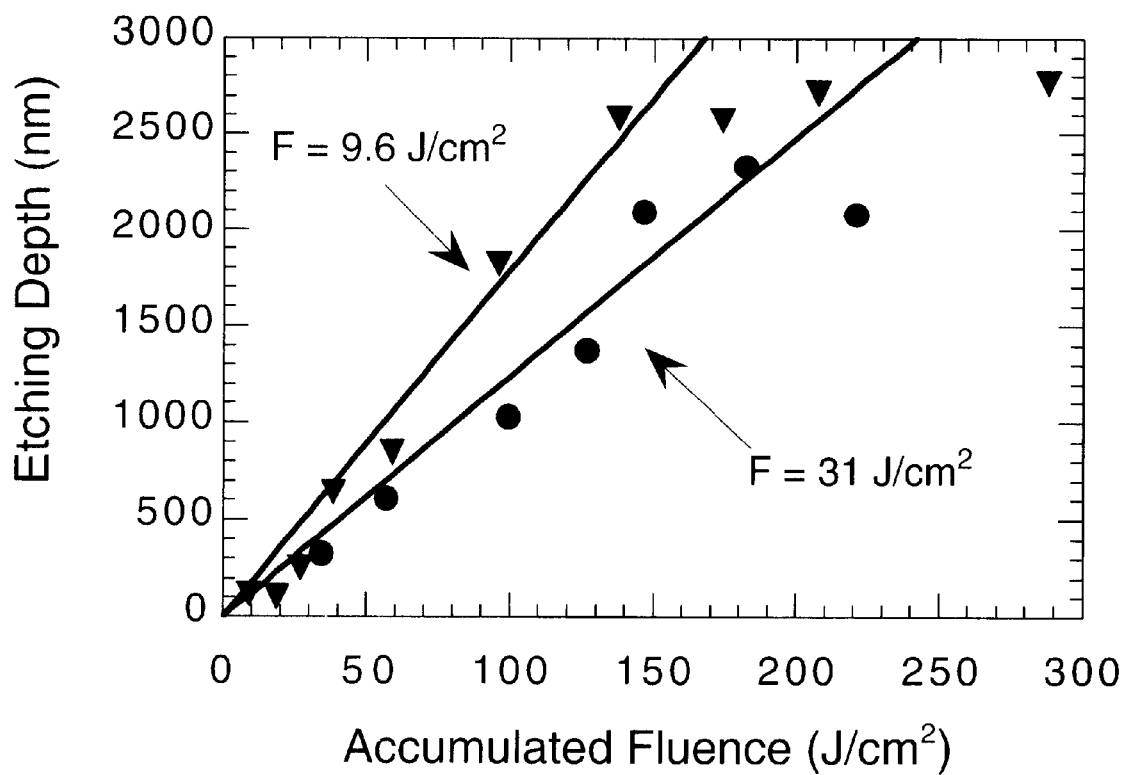
FIG. 2 shows a plot of excised hole depth as a function of accumulated laser fluence (i.e., number of laser pulses) for single-pulse fluences of 9.6 and 31 J/cm$^2$ using a Prior Art method.

FIG. 2 shows the progress of hole depth with the number of laser pulses, N, for fluence values of 9.6 and 38 J/cm$^2$. (Accumulated fluence was used for the abscissa to better account for the ±10% variations of the laser energy). For 9.6 J/cm$^2$ [38 J/cm$^2$], the depth increases linearly with N, or accumulated fluence, to an apparent peak value of 2.7 µm [2.2 µm] after 14 [6] pulses. The nominal plateau apparent for higher pulse-number is simply an artifact of the AFM tip, which cannot probe larger aspect-ratio holes, those deeper than their ~2 µm diameter. It is anticipated that the hole depth will in fact rise linearly with number of laser pulses through and beyond this plateau region until incubation processes raise the density of defects or color centers to a critical value. At fluences beyond this critical value, the 'gentle' ablation process is expected to give way to 'strong' ablation, a distinct regime wherein etch rates (depth per pulse) can be increased more than 10 fold, see A. C. Tam, J. L. Brand, D. C. Cheng, and W. Zapka, *Appl. Phys. Lett.* 55, 2045 (1989). For fused silica, there have been reported etch rates of 550 nm per pulse when 100's of pulses at 1.3 ps duration were applied at 12 J/cm$^2$ fluence, see H. Varel, D. Ashkenasi, A. Rosenfeld, R. Herrmann, F. Noack, E. E. B. Campbell, *Appl. Phys. A* 62, 293 (1996). Their rate is triple this 180 nm/pulse rate for the same fluence, but with N<10. For reasons given below, the transition to strong ablation with increasing N was not studied here.

The etch-depth data in FIG. 2 show that material removal was initiated with the first laser pulse (N=1), for both 9.6 and 38 J/cm$^2$ fluences. Incubation effects developing at fluences before the onset of ablation were not studied in the present work although such effects are already anticipated below our single-pulse ablation threshold of ~5.5 J/cm$^2$. Kautek et al. reported the need for 7 incubation pulses before low-fluence (1 J/cm$^2$) ablation of barium-aluminum borosilicate glass could proceed with 50 fs laser pulses, see W. Kautek, J. Kruger, M. Lenzner, S. Sartania, C. Spielmann, and F. Krausz, *Appl. Phys. Lett.* 69, 3146 (1996). Such incubation processes are generally undesirable for practical applications, since they impair control of etching rates.

Figure 3:
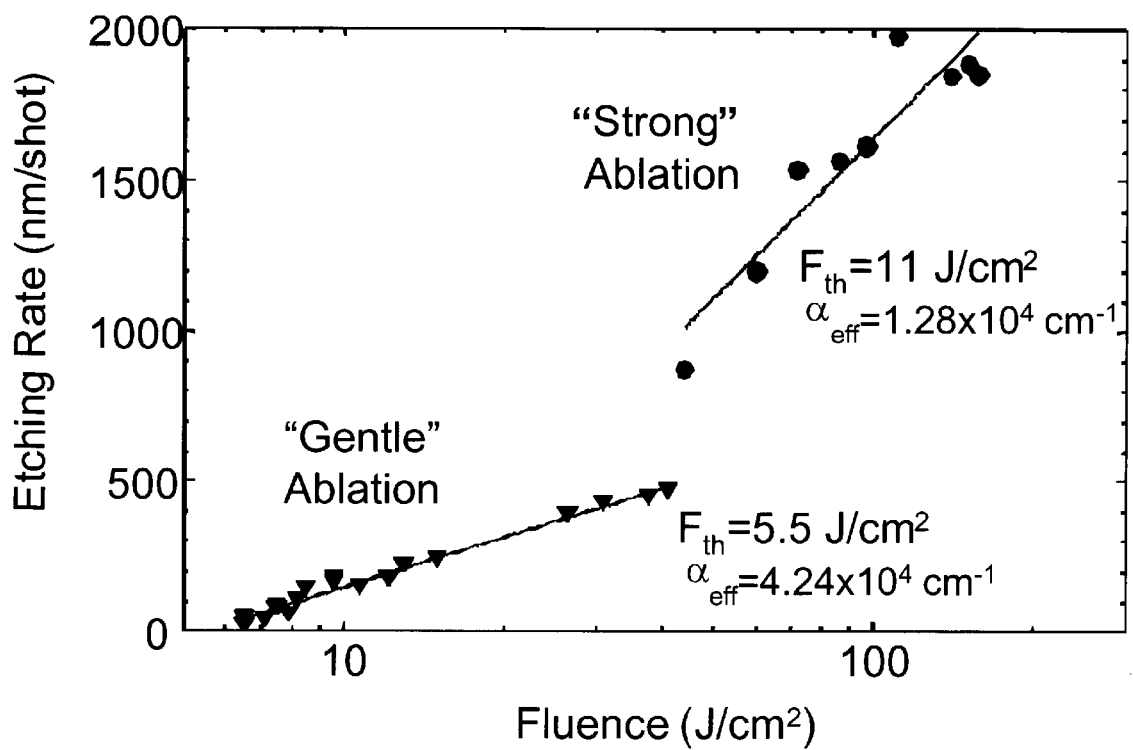
FIG. 3 shows a plot of etching depth per pulse in fused silica as a logarithmic function of laser fluence using a Prior Art method.

Single-pulse etch rates were collected from the slopes of data in graphs like FIG. 2 and plotted in FIG. 3 as a function of single-pulse fluence. Two regimes, gentle and strong ablation, are identified. Representation of the data (solid lines) by $(1/\alpha_{eff})$ log $(F/F_{th})$ provide values for threshold fluence and the effective absorption coefficient in each regime. The etch-rate data follow a logarithmic fluence-dependence from an extrapolated ablation threshold of 5.5 J/cm$^2$ to ~44 J/cm$^2$, the onset of strong ablation. This fluence window (5.5 to 45 J/cm$^2$) defines the gentle-ablation processing window for controllable etching of smooth features in fused silica. Thin layers, ~100 nm deep or less, could be accurately excised with appropriate choice of fluence. The logarithmic fluence dependence, normally associated with single-photon absorption mechanisms, is surprising here, considering the nonlinear mechanisms that are understood to drive absorption in this transparent material. Kautek et al. have also reported a logarithmic fluence dependence for 20-fs to 3-ps ablation of barium aluminum borosilicate glass (W. Kautek, J. Kruger, M. Lenzner, S. Sartania, C. Spielmann, and F. Krausz, *Appl. Phys. Lett.* 69, 3146 (1996)). For 1.2-ps ablation of fused silica, the slope of the solid curve in FIG. 3 (for F<44 J/cm$^2$) provides an effective penetration depth of $1/\alpha_{eff}$=235 nm, a value commensurate with the ~100-nm layer-by-layer resolution cited above. The 5.5 J/cm$^2$ threshold fluence is in accord with the damage threshold of 5±1 J/cm$^2$ reported by Varel et al. for 1.0-ps ablation of fused silica, see H. Varel, D. Ashkenasi, A. Rosenfeld, R. Herrmann, F. Noack, E. E. B. Campbell, *Appl. Phys. A* 62, 293 (1996). This group also report in a later paper, etch rates of ~200 nm/pulse with 3.2-ps pulses at 10 J/cm$^2$ fluence, see D. Ashkenasi, H. Varel, A. Rosenfeld, F. Noack, and E. E. B. Campbell, *Nucl. Instr. & Meth. in Phys. Res. B* 122, 359 (1997). This etch rate is only slightly larger than our 180 nm/pulse value from FIG. 3 for 1.2-ps pulses. Note again that the rates in FIG. 3 are only valid where the number of laser pulses is small. The onset of a strong ablation phase after 10's or 100's of laser pulses explains the 2 or 3-fold faster etch rates reported for ablation of deep channels in fused silica in D. Ashkenasi, H. Varel, A. Rosenfeld, M. Whamer and E. E. B. Campbell, *Appl. Phys. A* 65, 367 (1997).

At higher fluence, F>44 J/cm$^2$ in FIG. 3, etch rates abruptly rise to values 2- or 3-fold faster than by simple extrapolation of the gentle ablation data. This enhanced rate is related to the incubation phenomenon described previously where now a single pulse provides sufficient fluence to fully incubate the underlying glass material. The effective penetration depth rises to $1/\alpha_{eff}$=780 nm, supporting rapid etch rates of up to 2 μm per pulse at a fluence of ~150 J/cm$^2$. Such rapid etch rates are attractive for many applications, however, this strong-ablation regime provides less control over etch depth as evidenced by the wider scatter of data points in FIG. 3. A further disadvantage is the development of microcracks following 2 or 3 ablation pulses at high fluence as discussed below.

Figure 4A:
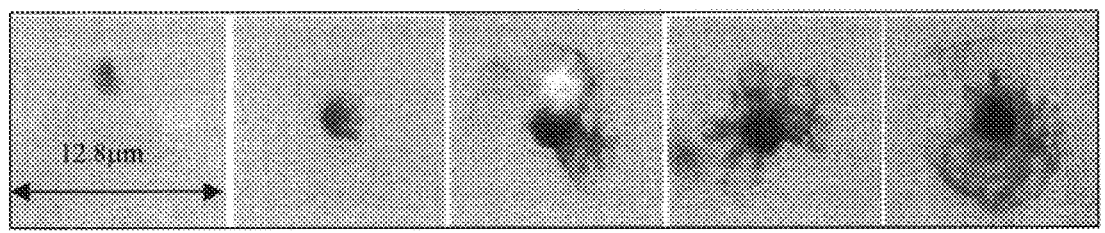
FIG. 4a shows a series of optical microscope photographs of fused silica ablated by 1.2 ps Nd:glass pulses at 140 J/cm$^2$, from left to right, holes were drilled by one, two, three, four, and five pulses using Prior Art methods.
Figure 4B:
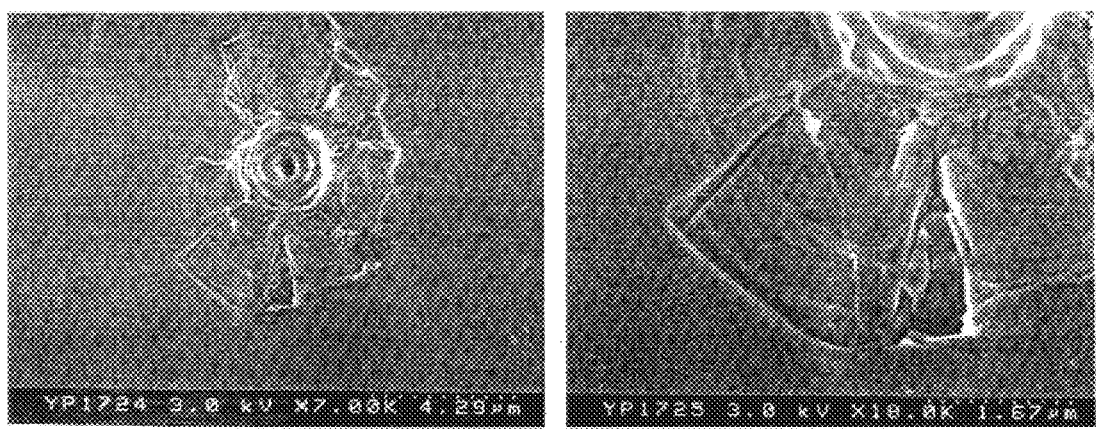
FIG. 4b shows two SEM photographs at two different maginifications of fused silica showing features of the shock-induced microcracks, the holes were ablated with four pulses at 93 J/cm$^2$ fluence (~0.06 Hz) using a Prior Art method.

While these low-repetition-rate ultrafast laser observations appear promising for controllable etching of optical materials, detrimental effects are noted. Most significant is the development of shock-induced microcracks, and shearing and flaking of surrounding surfaces following a small number of moderate-intensity pulses. FIGS. 4a and 4b shows the rapid development of shock-induced microcracks forming around the perimeter of laser-ablated holes. FIG. 4a shows a series of optical microscope photographs of fused silica ablated by 1.2 ps Nd:glass pulses at 140 J/cm$^2$, from left to right; holes were drilled by one, two, three, four, and five pulses. FIG. 4b shows two SEM photographs at two different magnifications of fused silica showing features of the shock-induced microcracks, the holes were ablated with four pulses at 93-J/cm$^2$ fluence (~0.06 Hz). Shock-induced microcracks developed quickly, by the third pulse, for this large fluence.

At the 140 J/cm$^2$ fluence, microcracks and surface swelling (noted by AFM and SEM) developed very quickly by the third laser pulse thus posing a significant limitation to precise shaping of smooth optical surfaces. At lower fluence, microcracking developed more slowly. Over the 5.5 to 170 J/cm$^2$ fluence-window studied here, these undesirable surface features appeared consistently after an onset number of laser pulses, $N_c$, that approximately followed $N_c$=1.7+80/F(F in J/cm$^2$).

Because these $N_c$ values are small, peaking at ~25 near the threshold fluence for the gentle ablation region, there was no practical reason for extending studies to integrate large numbers of pulses (N>60). Therefore, the transition from gentle ablation to strong ablation with increasing N was not observed here, preceded by the early development of microcracks, the main limitation to smooth surface-structuring of fused silica. D. Ashkenasi, H. Varel, A. Rosenfeld, M. Whamer and E. E. B. Campbell, *Appl. Phys. A* 65, 367 (1997) also reported the formation of microcracks around deep (~1 mm) channels etched in fused silica by hundreds of laser pulses of 100-fs to 30-ps duration. Their study showed a favorable trend of reduced microcracking with decreasing pulse duration.

Combination of $N_c$ in Equation 1 with the per-pulse-etch rates in FIG. 2 provides a coarse guide to the maximum ablation depth one can attain without deleterious microcracking or surface swelling phenomena. Structures up to ~1 μm deep with 10% rms surface roughness are shown here to be possible, establishing a practical but very restricted processing window for ultrafast-laser micromachining of fused silica and related transparent materials.

Burst Ultrafast Laser Processing of Materials

The method of high-repetition-rate ultrafast laser processing of materials in accordance with the present invention will be exemplified with two illustrative non-restrictive examples. Detailed examples are provided here for two classes of materials including brittle transparent glass and ductile metal aluminum. It will be understood that the principles demonstrated herein are extensible to a large range of material classes for broad application in ultrafast-laser material processing.

Laser Systems

For applications directed at material processing, ultrafast-laser systems presently available typically combine a mode-locked oscillator with an amplifier that raises the single-pulse energy to levels suitable for material modification. While such oscillators provide high repetition rates (~100 MHz continuous or in bursts), practical considerations in the amplifier power have precluded the amplification of every oscillator pulse. Only a small number of the oscillator pulses are amplified in ultrafast laser systems currently employed in material processing research and development (typically at rates of several Hz to ~1 kHz, and much less than 100 kHz). For these considerations, thermal diffusion between laser pulses at such low rates enjoys sufficient time to transport away most or all of any thermal energy deposited by the laser into the volume immediately surrounding the processing region, and to provide near-complete relaxation of other transient physical, chemical, or other changes brought on the by each laser pulse. Such heat transport cools the sample surface to that of the underlying bulk material before the arrival of the next ultrafast laser pulse; other physical and chemical properties and material parameters relax also to values similar to the underlying bulk material. Under these conditions, ultrashort laser pulses interact with materials that have mostly relaxed to the state of the underlying bulk material.

The present invention makes use of lasers in the high-repetition-rate ultrafast-laser processing of materials. The results described here are not particular to the laser system described below, but share a common physical process/interaction with all ultrafast laser systems operating at high repetition rate (>100 kHz).

A feedback-controlled Nd:glass oscillator ($\lambda$=1054 nm) operating at 1 Hz repetition rate provided a near flat-topped train of 430 mode-locked pulses (quasi cw) with pulse-to-pulse separation of 7.5 ns, see R. S. Marjoribanks, F. W. Budnik, L. Zhao, G. Kulcsár, M. Stanier, & J. Mihaychuk, *Optics Lett.* 18, 361 (1993). A single high-contrast pulse of 1.2 ps duration was selected by an external Pockels cell and amplified 13-fold in a four-pass geometry at ~0.06 Hz (limited by flashlamp pumping). The ~3 ~J pulses were focussed by interchangeable aspherical lenses (AR-coated BK7; f=15.4, 11.0, 4.5 and 3.1 mm) to near diffraction-limited spot sizes of 3.2, 2.0, 1.0, and 0.8 μm (1/e$^2$) diameter, respectively.

The test samples (UV-grade fused silica Corning 7940; BK7 glass, aluminum foil) were mounted on a precision x-y-z stage. Focussing was monitored by image-relaying the retro-reflected beam from the focal spot, with magnification, onto a CCD camera. On-target fluence was varied over the range 2 to 170 J/cm$^2$ by adjusting the amplifier gain, using neutral density filters, and employing different focal-length lenses. Excisions were made using between 1 and ~100 pulses, of various fluence values. All samples were irradiated in air, and transverse nitrogen gas flow was at times used to reduce the accumulation of ablation debris. Self-focusing effects in air were not seen, at this pulse duration, peak power, and with the short focal-length lenses used. Laser focussing conditions also did not produce bulk discoloration or damage effects in glass regions beneath the excised holes (as evidenced by optical microscopy).

The burst mode was provided by a waveplate which passed the full oscillator train of several hundred pulses for high-repetition-rate machining at 133 MHz. The ~3 µs long pulse train was amplified and focussed onto glass or metal surfaces as described above, accumulating a total fluence of ~40 kJ/cm² in a diameter of ~2 µm. The burst duration was varied from ~250 to 430 pulses. The resulting ultra-high repetition rate (133 MHz) pulsetrain had a nearly flat waveform, with a risetime of about 100 ns and a falltime of about 500 ns. With the four-pass amplifier optional, pulsetrain energies of 0.05 to 2 mJ were available for all studies.

This particular beam focusing and alignment arrangement is only one approach amongst many for delivering ultrafast pulsetrain 'bursts' to a sample, and is not a pre-condition for applicability of the present invention. The advantages of high-repetition rate ultrashort laser processing can be accessed by any beam-shaping and optical delivery system that brings an appropriate fluence dose to the sample.

By employing various electrooptic devices, and alternative cavity and/or amplifier designs, tuning of the single-pulse duration, pulse-to-pulse separation, number of pulses per pulsetrain burse (up to cw operation), and the temporal profile of the burst envelope becomes available to optimize and control the laser-material interaction and subsequent processes in the sample material.

Other embodiments of 'burst' type ultrashort lasers are possible. The Coherent (USA) Model MIRA Optima 900F provides 76 MHz continuous output of ~100 fs pulses at ~1 W power, yielding a pulse energy of 13 nJ which is sufficient under tight focus to modify certain materials. The Coherent (USA) Model Reg A 9000 offers microjoule energy in ~100 fs pulses at repetition rates adjustable up to 300 kHz. IMRA (USA) has developed but not commercialized laser systems offering higher rates (>1 MHz) and similar pulse energies. High Q Lasers (Germany) offers a Nd:Van laser producing 100 nJ pulses of 7 ps duration at 10 W power and ~100 nJ energy per pulse. These and other commercial laser systems could exploit the benefits of the present invention.

As used herein, the term "Interaction geometry" means those aspects of the initial geometry (e.g. dimensional proportions, relationship to unheated material) of the laser-heated material that affect the evolution of the heated material. With subtle exceptions, the rate of volume expansion defines the rate of dissipation of the plasma plume. A plasma having dimensions x by y by z will have a volume $V=x*y*z$. The evolution of the plasma in each dimension therefore determines the evolution of the volume. There are several cases to consider.

i) Focussing onto the surface of a material. Expanding freely in each dimension, the plasma may grow equally in each direction in absolute dimension. For those dimensions which are already large, this will be a tiny relative change; for those dimensions which are tiny, this will be an enormous relative change. Therefore the relative rate of volume change depends on the aspect ratio (width to thickness) of the heated zone:

a) large focal spot: a large flat layer, thin in 'z'—there is little relative change in x and y, though z may quickly double; volume expands proportional to elapsed time;

b) line focus: a thin layer long in one dimension and tiny in the other two will expand cylindrically: there is little relative change in x, though y and z may quickly double; volume expands proportional to square of elapsed time;

c) point focus: a thin layer tiny in x and y—will expand spherically: x, y and z may each quickly double; volume expands proportional to cube of elapsed time.

ii) Focussing within a channel, deep hole or via. The material geometry around the plasma plume restricts expansion to one dimension, down the channel. Volume expands proportional to time.

iii) Focussing within bulk of material. The material geometry around the plasma plume inhibits expansion in all directions. The characteristic time for dissipation, a determinative factor for Δt in this invention, is here determined e.g. by the physics of shock formation, cavitation, and thermal and radiative dissipation. This may be a substantially longer time than previously, as for example in transparent biological tissues, or it may be comparable to, or shorter than, hydrodynamic times of free-expansion.

The present invention will now be illustrated with the following non-limiting examples.

EXAMPLE 1

Burst Ultrafast Processing of Glass

Figure 5:
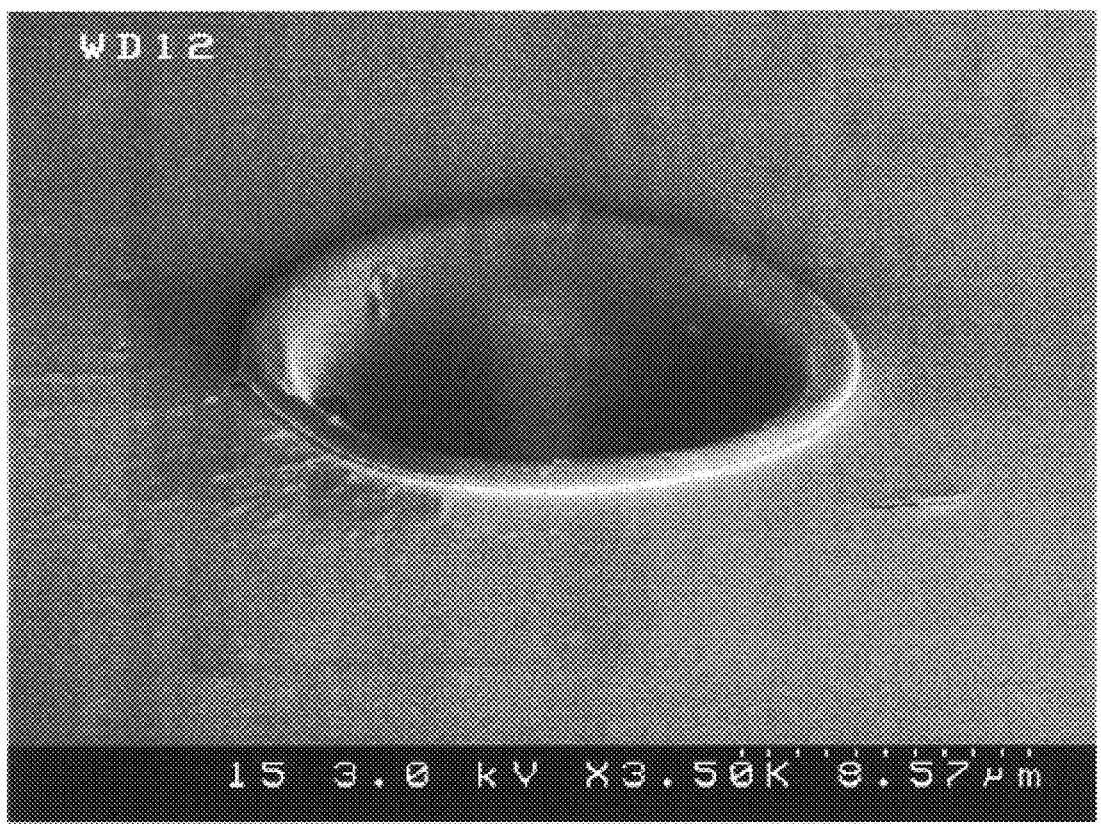
FIG. 5 shows an SEM angle view of hole excised in BK7 glass by a mode-locked pulse train consisting of ~250 single 1.2 ps laser pulses with a pulse-to-pulse separation of 7.5 ns.

The full oscillator pulse train comprising between ~250 and 400 pulses of 1.2-ps duration, at 5 to 150 J/cm² fluence each, was applied to fused silica and BK7 surfaces. The pulse train could be flat-topped, or shaped to improve control of the laser interaction with the material. The SEM photo in FIG. 5 shows a high aspect-ratio via, or through-hole, formed as a result of this single pulse-train burst. A smooth symmetric hole of ~10 µm diameter was excised to 15 µm depth (determined with optical microscopy). The ~15 µm deep hole has smooth walls and shows no evidence of fractures, cracks, or collateral damage. Only a small mount of ejected melt has solidified on the entrance hole perimeter. The entrance hole diameter of ~14 µm exceeds the focused laser beam diameter of ~1.8 microns. The burst energy was 1.48 mJ and the total (integrated) fluence was ~49 kJ/cm².

In comparison, the low repetition rate (1-Hz) result described in the previous section showed that microcracks formed after only 3 pulses for the same single-pulse fluence. Cumulative heating effects associated with the 133-MHz pulse-repetition rate in the pulse train are believed to improve the ductility of the surrounding glass, thereby mitigating the shock-induced microcracking in regions immediately surrounding the hole perimeter. Such low-grade heating effects also support an annealing effect, by which stresses incorporated into the material by thermal cycling are relieved. Heat incompletely dissipated on a nanosecond time-scale may account, in part, for the enlargement of hole diameters to 8–10 µm which is ~5× larger than the diameter of the focused laser beam. For fluences well above threshold, ablation also extends appreciably into the weaker edges of the Gaussian beam. In the operation of the feedback-controlled mode-locked oscillator, the first dozen pulses at the leading edges of the train are also somewhat longer-duration (~10 ps); possibly this may also have an effect.

Figure 6:
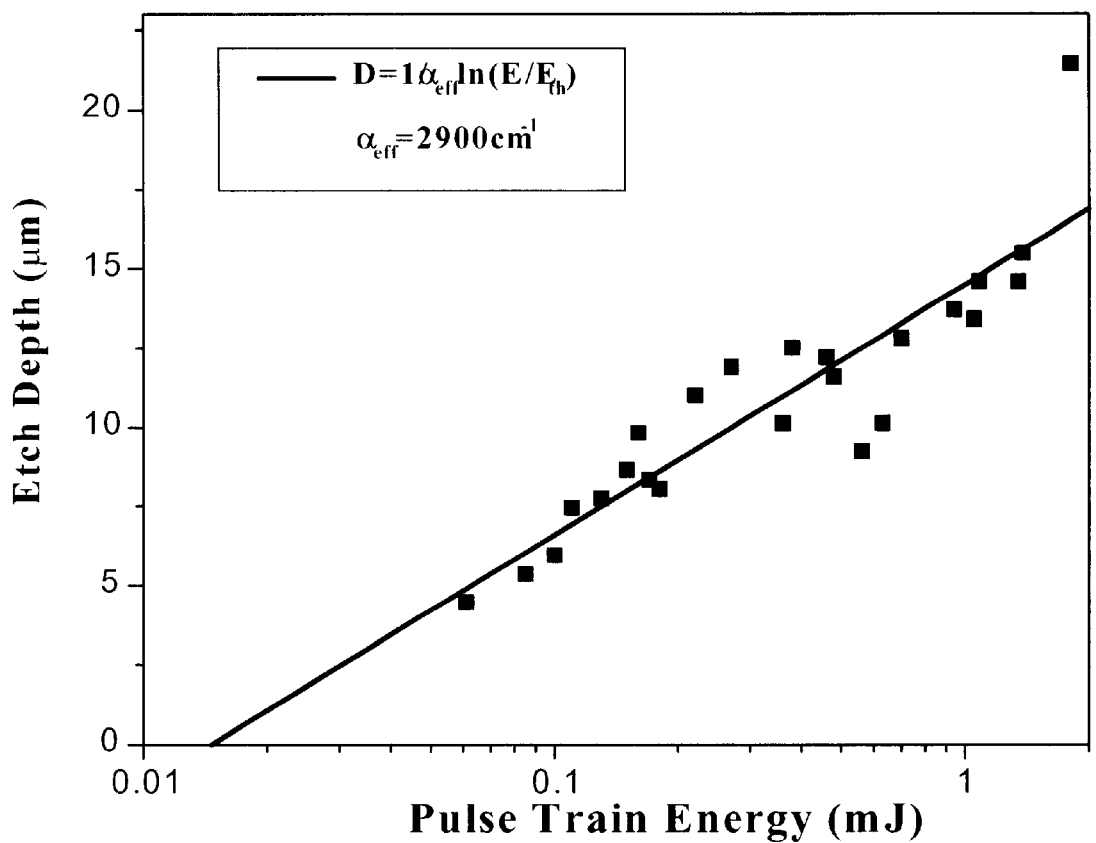
FIG. 6 shows etch depth in BK7 glass plotted as a logarithmic function of the total burst laser energy.

Etch depths excised in BK7 are plotted in FIG. 6 as a function of total energy in the 250-pulse envelope. A single train of ~250 pulses of 1.2 ps duration each with a pulse-to-pulse separation of 7.5 ns was applied. Single bursts were applied to one surface of a 90° prism and etched depths were measure from the adjacent surface with an optical microscope. The data are coarsely represented by a logarithmic energy dependence with an extrapolated ablation threshold of ~15 µJ energy or 500 J/cm² fluence and an effective absorption coefficient of 2900 cm⁻¹ (from the inverse slope). The latter value yields an effective optical penetration depth of 3.4 µm for the full train of pulses, a value 4-fold [15-fold]

larger than the corresponding value for strong [gentle] single-pulse ablation regime in FIG. 3 for fused silica.

Multiple pulsetrain bursts were applied to fused silica at 1-Hz repetition rate, resulting in a slight increase (~20%) in hole diameter and a moderate advance in etch depth to several 10's of microns. Deeper holes are anticipated with modification of the laser parameters and the focusing geometry. Hole depth saturated quickly for 100-J/cm$^2$ single-pulse fluence. Saturation of hole depth when drilling deep channels in fused silica with femtosecond and picosecond laser pulses at 10–1000 Hz repetition rate has been previously reported, see D. Ashkenasi, H. Varel, A. Rosenfeld, M. Whamer and E. E. B. Campbell, *Appl. Phys. A* 65, 367 (1997). However, unlike these lower repetition rate results, the application of many bursts in the method disclosed herein has not led to the formation of microcracks, fractures, or swelling for any samples in the present work, an unanticipated and important advantage for shaping smooth surface structures, especially high aspect ratio holes and blind vias.

High repetition-rate multi-pulse ablation disclosed herein is clearly a promising new option for controlling the micromachining quality of brittle materials. The 7.5-ns pulse-to-pulse separation used herein is sufficiently short to reduce the material cooling between laser pulses, thereby permitting the presentation of a heated and more ductile glass to succeeding laser pulses in the small processing volume. During the 7.5-ns interval between pulses, the thermal diffusion scale length, $(4D_\tau)^{1/2}$, is ~0.17 $\mu$m in glass, a value significantly comparable with the effective optical penetration depth of 0.25 $\mu$m in the single-pulse gentle ablation regime (FIG. 3). Since the plume will carry not all absorbed laser energy away, retention of this dissipated energy within a scale length comparable with the laser penetration depth ensures that subsequent laser pulses interact with a thermally modified glass while minimizing the heat-affected zone. An important additional consideration of the pulse-to-pulse separation is to provide sufficient time for hydrodynamic expansion and dispersion of the laser-produced plume and plasma, reducing or eliminating obscuration of subsequent laser pulses. This is an important benefit that retains the advantages of ultrafast-laser material processing (i.e., laser dissipation in the bulk material) while also offering control of the heat retained in the nearby laser-interaction volume of the material. The pulse-to-pulse separation becomes an important new optimization parameter, controlling the amount of laser-generated heat retained in the sample (higher temperature when reduced) and the amount of laser energy lost to absorption and scattering in an incompletely dissipated plume (less loss when increased). This control and these general advantages are available to brittle materials in general, and include but not limited to glasses, crystals, ceramics, tooth enamel, bone, and composite materials for a wide range of applications.

EXAMPLE 2
Burst Ultrafast Processing of Aluminum

High-repetition rate burst machining was applied to aluminum (Goodfellow, 99%) foils of thicknesses of 12.5, 25, 50, 100 and 200 $\mu$m. Samples were mounted free-standing to preclude effects of heat conduction into any substrate. A photodiode was placed directly behind the foil to signal the laser burnthrough of the foil. On-target laser energy was controlled by neutral density filters and amplifier gain. Ablated surfaces were examined by scanning electron microscopy (SEM), atomic-force microscopy (AFM), and optical microscopy.

Figure 7:
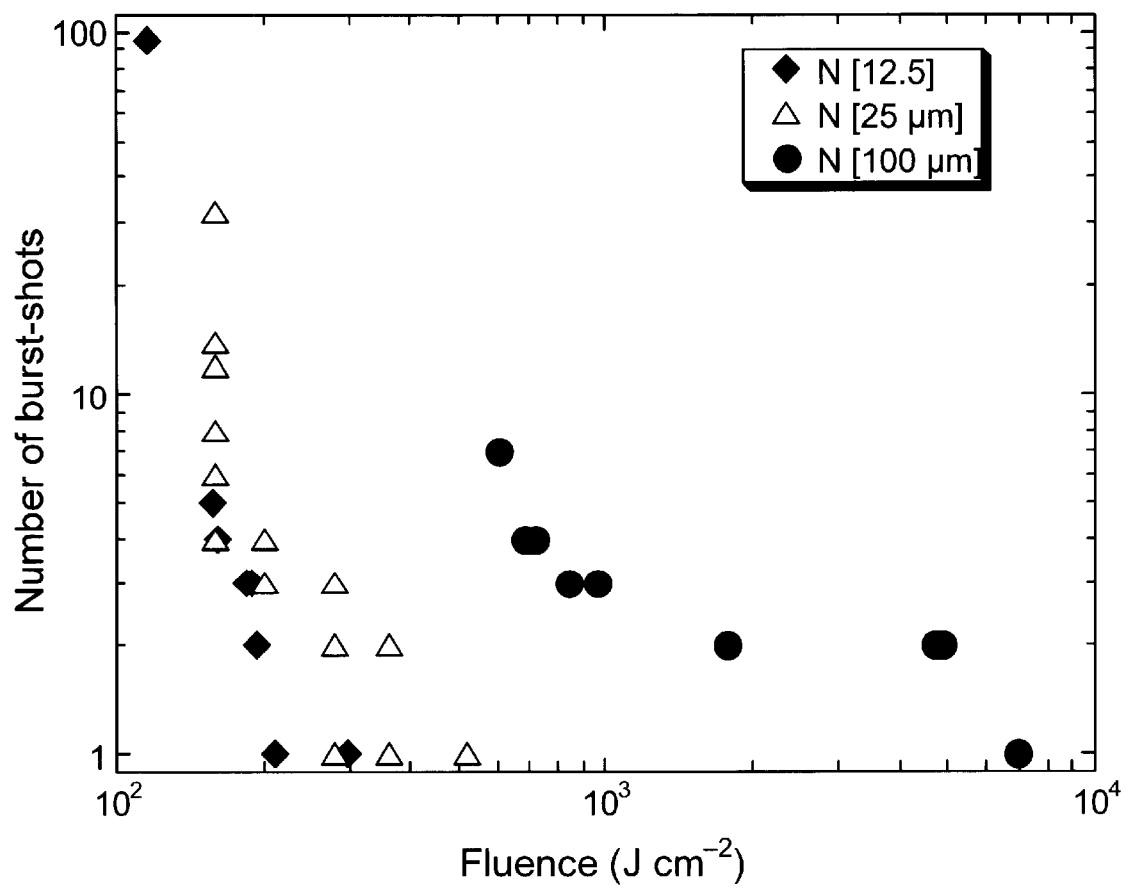
FIG. 7 shows the number of shots (pulse-trains) to drill through aluminum foils of 12.5 μm, 25 μm and 100 μm thickness as a function of the pulse-train fluence.

The number of laser pulses necessary to drill through 12.5 $\mu$m, 25 $\mu$m and 100 $\mu$m foils are plotted in FIG. 7, as a function of pulse-train fluence. The fluence values are divided by 250 to obtain the single 1.2 ps pulse fluence. A large fluence range of 80 to 9000 J/cm$^2$ was examined. Qualitatively, the ablation behaves as expected: the minimum number of bursts required to drill through a foil increases with increasing foil thickness and decreases with increasing fluence. For each thickness there was a threshold fluence below which the target could not be pierced by even a hundred shots, even though this fluence was itself well above the damage threshold at the surface. This is understood to be related to a reduction of etch rate with depth. In the measurements disclosed herein this piercing threshold increases with foil thickness, from ~120 J/cm$^2$ for 12.5 $\mu$m foils to 600 J/cm$^2$ for 100 $\mu$m foils. This ~5-fold difference in threshold is attributed, in part, to distributed absorption of laser energy along the length of increasingly deep channels. The inventors have observed that the coherence-degradation effect of imperfect waveguiding in the multimode-sized channels also reduces laser intensity at the hole-bottom. Such losses raise the material-removal threshold fluence as increasingly deeper channels are bored out by the laser. Beyond a maximum fluence of ~200, 300, and 7000 J/cm$^2$ for 12.5, 25, and 100 $\mu$m foils, respectively, single bursts will cut through the foil. Except for single-shot piercing data, pulse-to-pulse energy fluctuations of ~30% lead to a scatter of data points especially near the through-hole fluence threshold.

Figure 8:
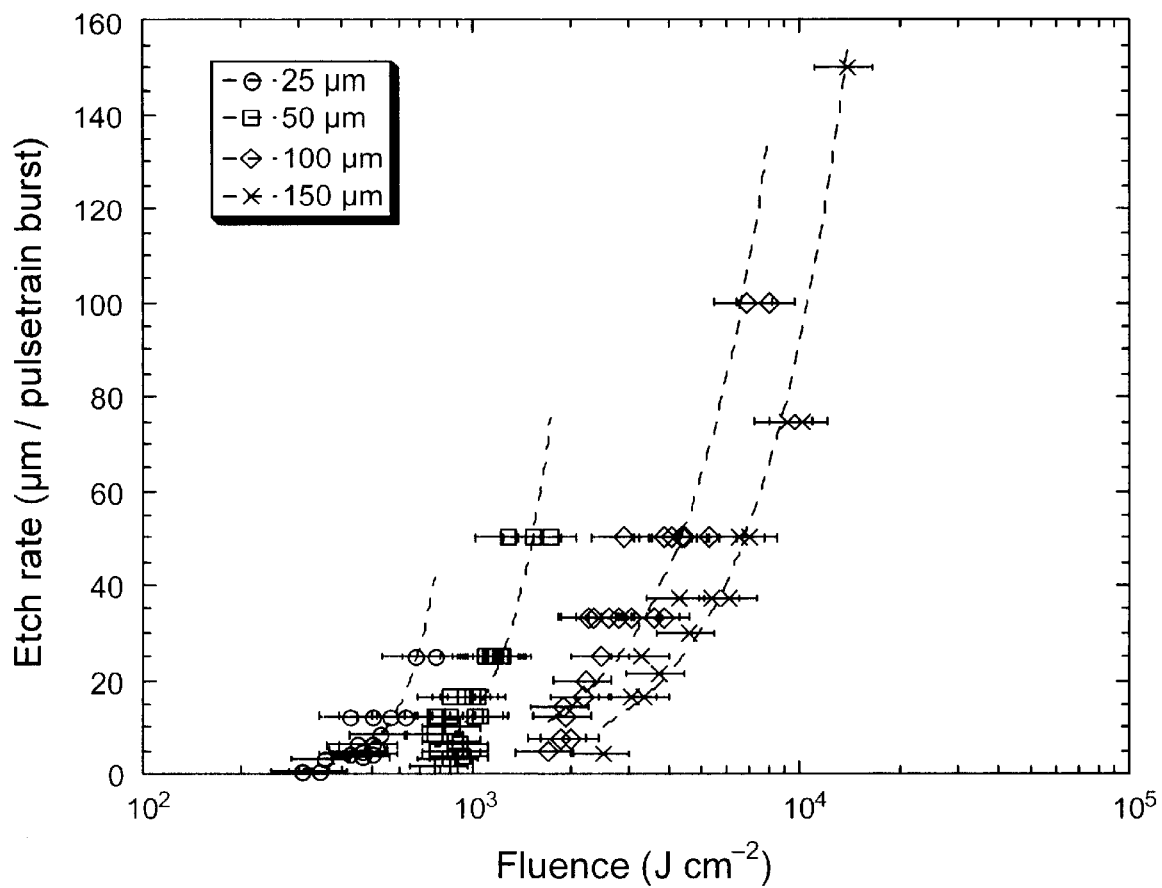
FIG. 8 shows etch rates per pulse-train burst as a function of the burst fluence for various foil thicknesses of aluminum.

Burnthrough etch-rate data are presented in FIG. 8 for each of the foil thicknesses tested. Etch depths were interpreted from graphs such as FIG. 7, identifying the minimum fluence necessary to reproducibly punch through the foil for a given number of pulses, then plotting against that fluence the average etch rate per pulse (from the foil thickness and number of pulses to pierce). All foils except the 200 $\mu$m thickness could be consistently drilled through with a single pulsetrain burst for the present laser configuration. The etch-depth data are strongly dependent on foil thickness.

Figure 9:
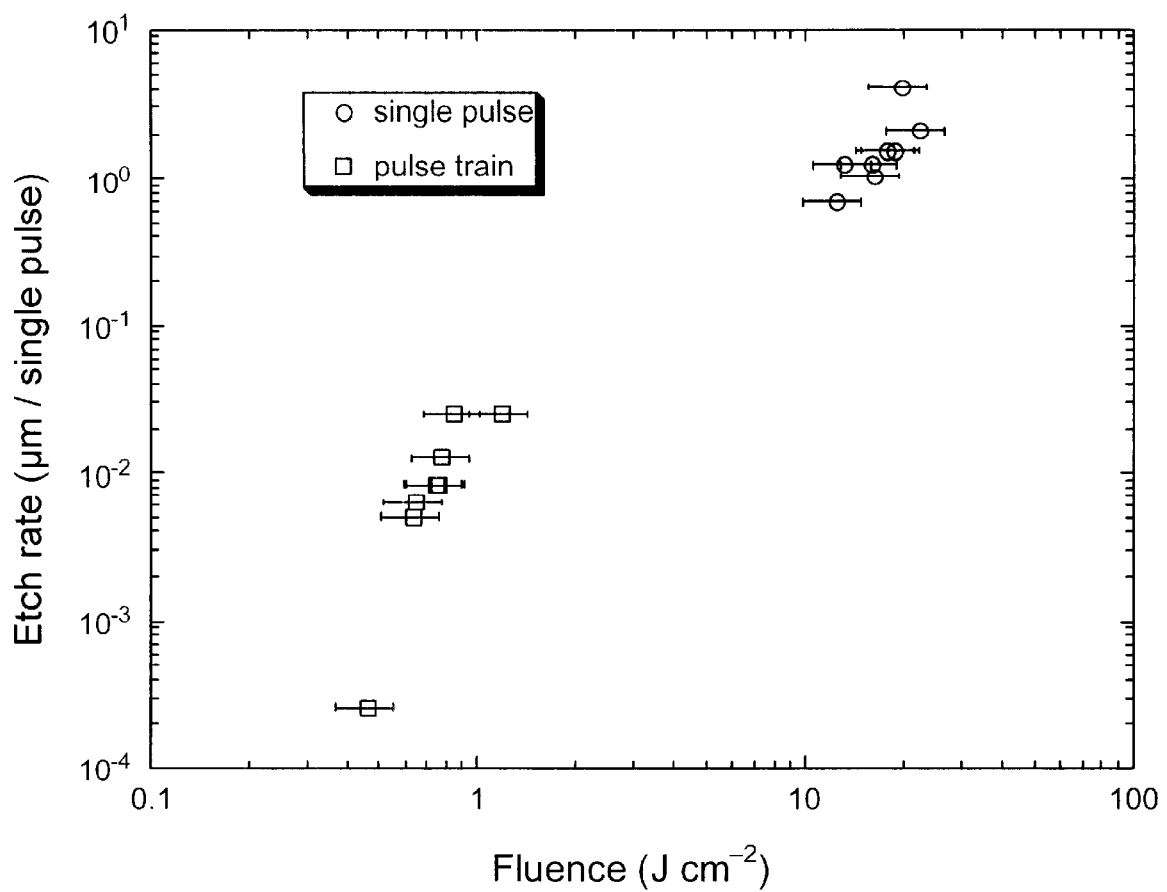
FIG. 9 shows the etch rate per individual picosecond pulse as a function of the single pulse fluence for 12.5 µm thick aluminum foil, the circles for individual pulses within the pulse-train and the squares for an isolated single pulse.

FIG. 9 compares the average value of single-pulse etch rates in various foil thickness when applied as isolated pulses (squares) at <1 Hz repetition rate and as part of a burst train at 133 MHz repetititon rate. Clearly evident is the need for much large single-pulse fluence, greater than 10 J/cm$^2$, to eventually cut through the foils compared with fluences of only several 100 mJ/cm$^2$ when the pulses are part of a high-frequency pulse train. Burst-mode machining offers a new means for rapid etching through metallic materials.

Figure 10A:
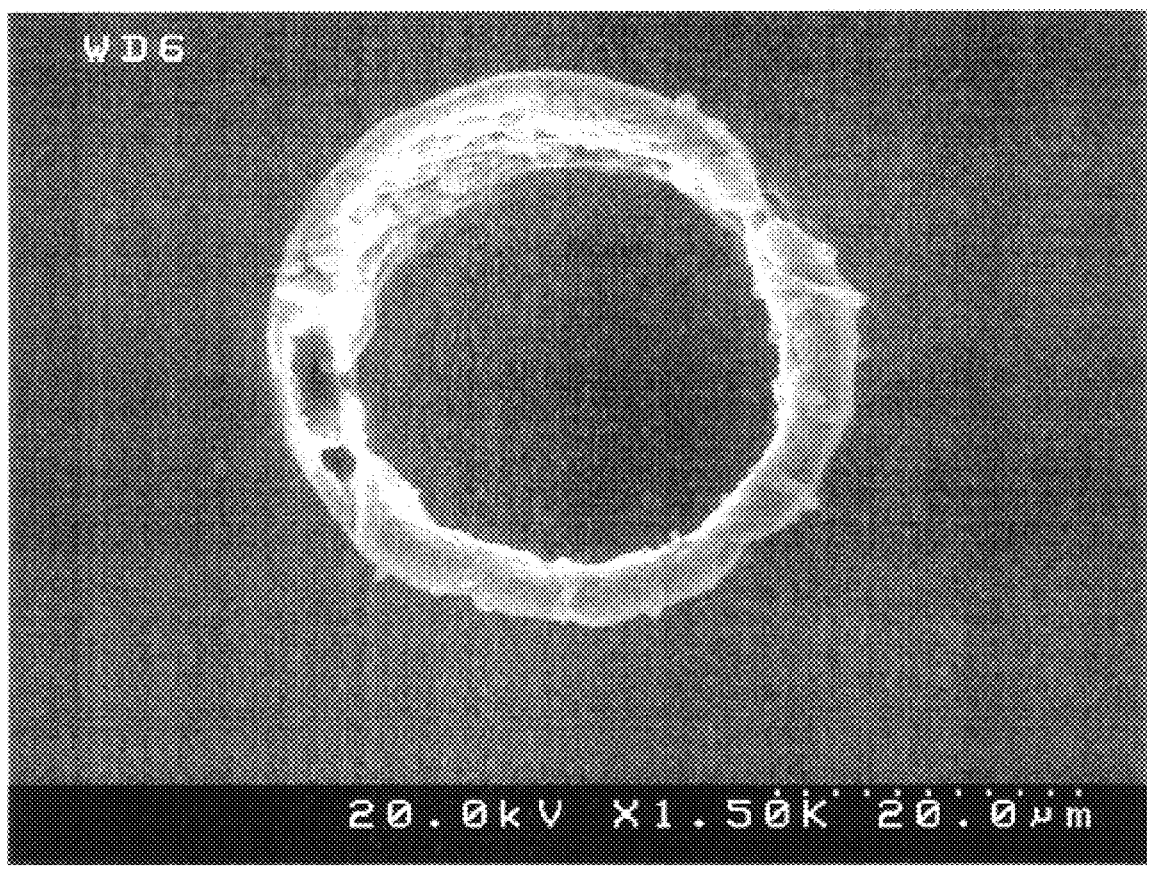
FIG. 10a shows an SEM photograph of a hole drilled through 200 µm thick aluminum foil (laser-irradiated surface) with one pulse-train burst at 3.16 kJ/cm$^2$ fluence.

FIG. 10 shows SEM photographs of the front (10a) and the back (10b) surfaces of the 200 $\mu$m foil that was drilled with one burst at 3.16 kJ/cm$^2$. The hole perimeter is relatively clean at both surfaces with only a thin (~3 $\mu$m) wide rim of melt splattered around the entrance hole. No optimization effort was made to minimize this splatter. The entrance hole diameter of 30 $\mu$m reduces to 7.5 $\mu$m at the backside, yielding a 7:1 aspect-ratio hole with tapered sides at ~3° on either side of target normal. The aspect ratio could be adjusted with changes to the laser fluence and focussing conditions.

Figure 11A:
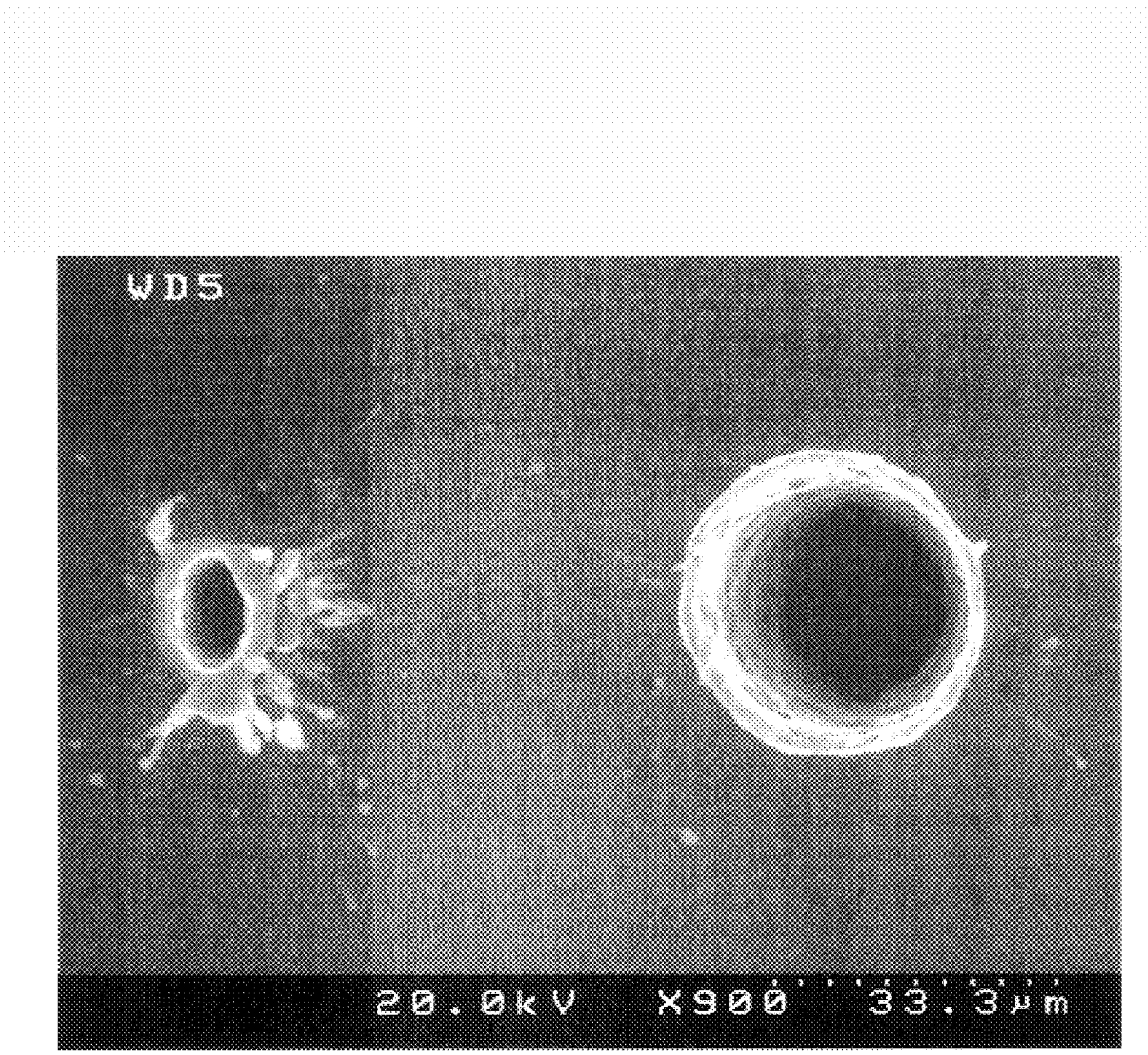
FIG. 11a shows an SEM photograph of laser irradiated surfaces comparing two holes drilled through a 50 µm thick aluminum foil: left hole: fluence 480 J/cm$^2$, three bursts followed by one 'cleaning' shot; right hole: fluence 5.36 kJ/cm$^2$, one shot plus one 'cleaning' shot.
Figure 11B:

FIG. 11 illustrates the influence of the laser fluence on the hole diameter. The left hole in FIG. 11a was drilled with three pulse-train bursts, each at a fluence of 480 J/cm$^2$, followed by a fourth shot of the same fluence to trim the hole of any melt/flow irregularities inside. The entrance hole diameter is ~6 $\mu$m which corresponds closely to the 5.6 $\mu$m laser-beam diameter. A comparatively large amount of re-solidified material is also seen to surround the hole perimeter. The laser fluence is only ~50% above the minimum fluence required to produce a through-hole for this case (240 J/cm$^2$) and melt processes appear to reduce the hole quality. Note that this laser fluence is approximately an order of magnitude above the surface damage threshold. A SEM photo of the rear side of this through-hole is shown on the right in FIG. 11b.

Figure 10B:
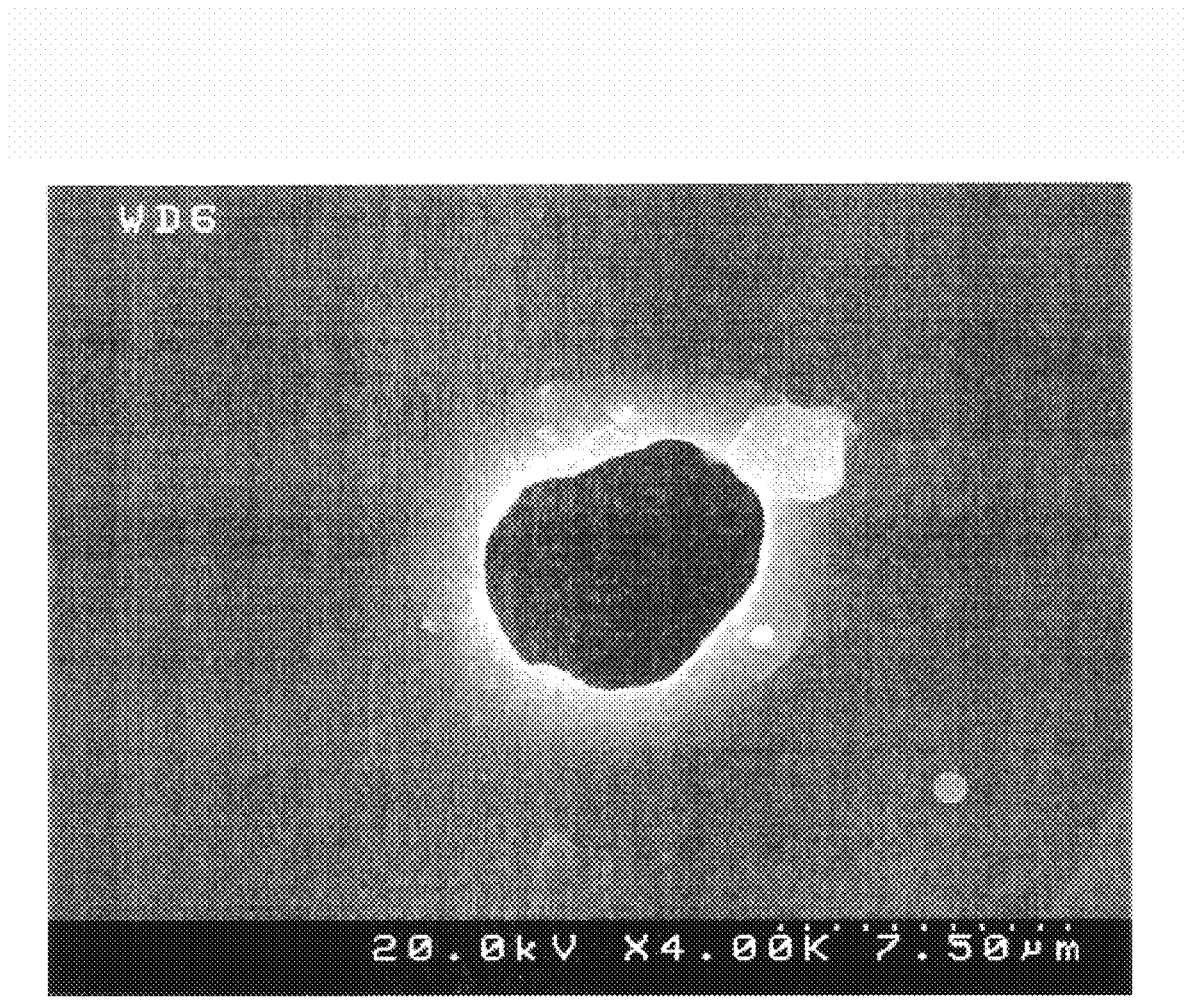
FIG. 10b shows an SEM photograph of a hole drilled through 200 µm thick aluminum foil (rear surface) with one pulse-train burst at 3.16 kJ/cm$^2$ fluence.
Figure 12:
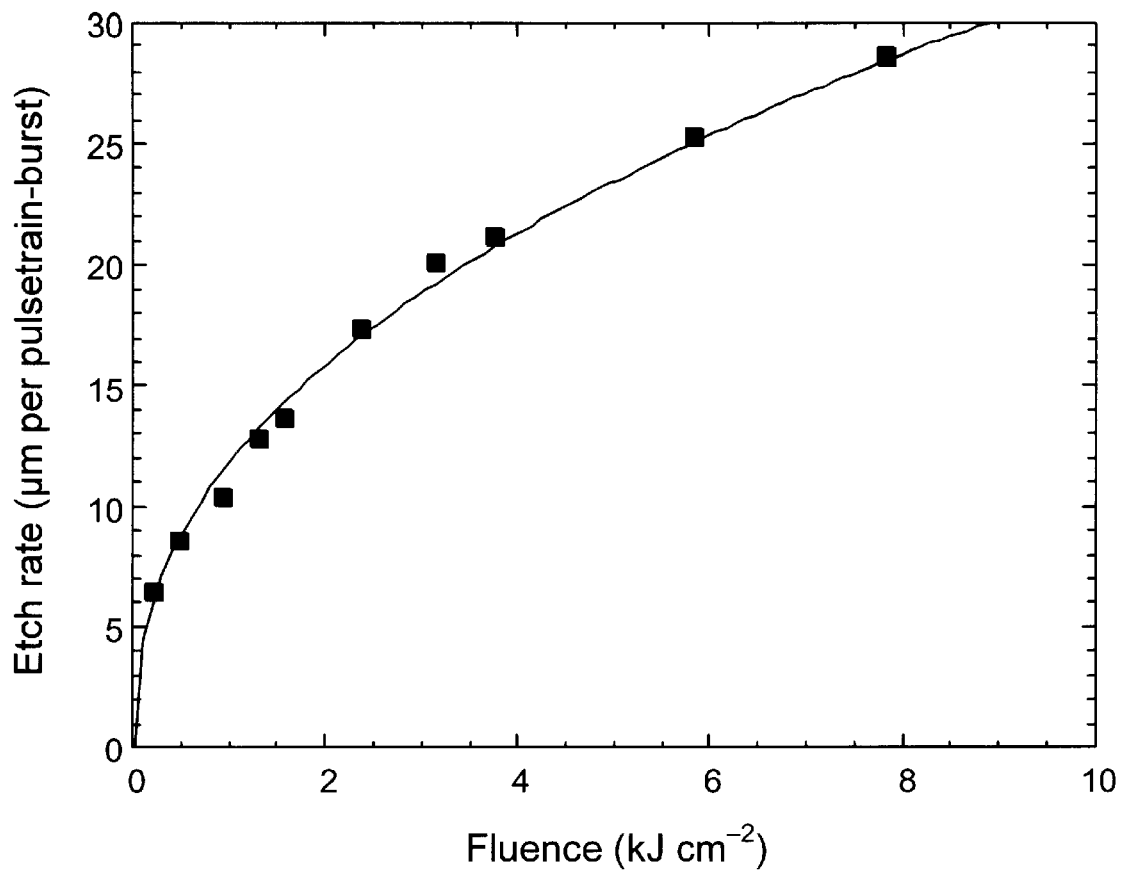
FIG. 12 shows a plot of observed hole-sizes machined through 100 µm thick aluminum foil, as a function of fluence.

The right hole in FIG. 11a was drilled with a single burst at a fluence of ~5.36 kJ/cm$^2$, followed by an additional shot to clean out the drilled hole of debris. The 11-fold higher fluence produced a larger hole diameter of ~30 μm, about 5 times the laser focal spot size (FWHM) and producing a hole 25 times the area. The rear side of the hole, shown on the left in FIG. 10b, is also much larger (~20 μm) in diameter than the lower-fluence example. Assuming linear absorption, the increase in hole diameter is commensurate with the increase in laser power: for a Gaussian profile, the intensity of the laser has near the same value at the hole-edge in each case. This argues for a local threshold effect, such as the specific energy in the target material passing that amount needed for melting. Thermal transport could also play a role in increasing the hole size. FIG. 12 shows how the diameter d of the hole produced in a 100 μm-thick aluminum foil by pulsetrain-burst machining increases with fluence F. The fitted line shows a power-law dependence of $d=12(F)^{0.43}$. Since the radius of a point at constant fluence increases proportionally to $(\log F)^{0.5}$, this different observed functional dependence illustrates that nonlocal issues, such as heat transport, are significant in determining hole size. FIGS. 10, 11 and 12 together demonstrate control over hole diameter, morphology, hole smoothness and quality, and aspect ratio with laser fluence in burst laser machining of metal foils.

The absence of substantial melt debris, especially for fluences 10× to 10× above the surface-damage threshold, demonstrates that long-pulse physics dominated by melt-phase material ejection is not taking place here. However, during such a microsecond pulse-train, heat will have diffused into the material surrounding the laser spot in a manner similar to that described above for the glass studies. A simple consideration of the thermal diffusion length, $(4D_\tau)^{1/2}$ provides a heat scale-length of a fraction of a micron for the 7.5 ns interval between picosecond pulses in the train, and 28 μm over the whole 2 μs pulse-burst. While this scale-length can be misleading as a rule-of-thumb in assessing the hole diameter, it demonstrates a compact scale length over which heated material is presented to each ultrafast pulse within the train. At or below 100 kHz repetition rates, much of the heat retained by the sample will have diffused into the underlying bulk material, lowering the sample surface temperature to that of the bulk. The transitional pulsetrain repetition-rate for such cooling will vary with the material's optical and thermal properties, the beam diameter, and the energy delivered to the sample by an individual pulse. At 133 MHz, the ultrafast interaction takes place within a heated zone of the material left behind by preceding pulses. In this way, deeper channels can be excised because of a reduced ablation threshold, improving the energy efficiency of the material removal. Through-holes can excised in thick foils with single bursts, greatly improving machining time over that provided by traditional sub-MHz lasers. The thermal component also affords control over the diameter and aspect ratio of the hole. These benefits are in addition to those normally associated with ultrafast laser processing, a constitute a part of the present invention.

The thermal physics of pulse-train burst interaction is therefore intermediate between that of single long-duration and ultrafast pulses. It appears that there are some advantages of heating or annealing surrounding material without the gross melting characteristic of longer-duration pulses.

Likely this is because ultrafast laser pulses have the advantage of evaporative cooling, over a hydrodynamic timescale of the expanding plume, as the locally heated material vaporizes and expands away from the solid, decoupling from it thermally. In this case, much of the heat impulse of an ultrafast laser pulse is carried away with the plume/plasma, producing etching more similar to material sublimation than is possible for quasi-cw machining. As a result, the characteristic heating time is limited to the timescale of hydrodynamic expansion of the thin heated layer (and evaporative cooling). For this reason, it appears that the etched hole-size is fairly closely linked to the local specific energy deposition by the laser, as it compares to the specific energy of vaporization, and less by lateral thermal transport.

Figure 13:
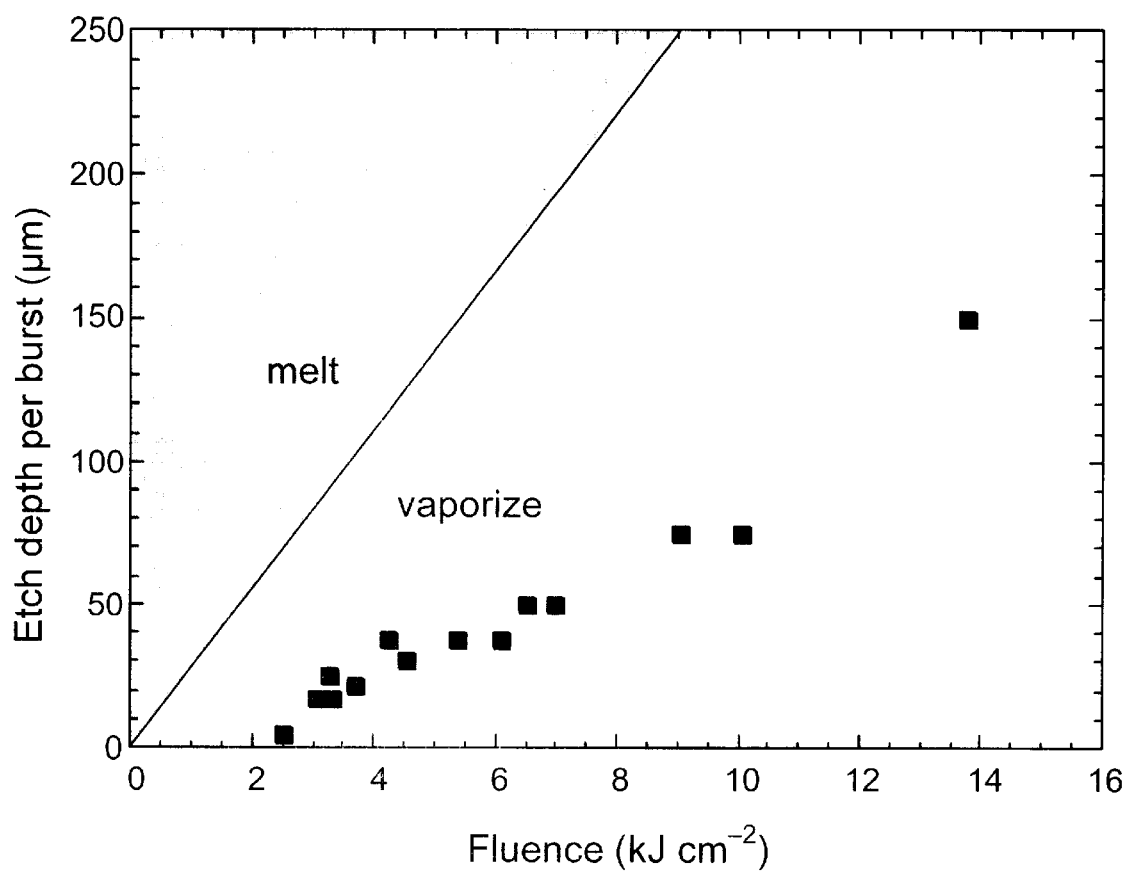
FIG. 13 shows a plot of observed etch-depths into a 150 µm, foil, compared to calculated vaporization depth.

This is supported by the results of FIG. 13. FIG. 13 shows a plot of average observed etch rates for cutting through a 150 μm foil, compared to putative vaporization depth. The solid line marks the deepest holes possible, by thermodynamic arguments, if 10% of the incident laser energy were invested in vaporizing the material directly underlying the focal spot, i.e., without considering any lateral-transport effects. Vaporization of aluminum will take place with an energy investment of ~36 kJ/cm$^3$ (including thermal capacity, heat of fusion, and heat of vaporization). Setting aside the laser absorption efficiency, this value can be used to determine the maximum depth attainable by evaporative ablation, D, as a function of fluence: $D=F/(3.6 \text{ J/cm}^2 \, \mu^{-1})$. Since all the data of FIG. 13 fall below this curve, we see that mode-locked laser bursts nominally can provide more than adequate fluence to vaporize aluminum to the observed depths. Even with 10% absorption, this construct overestimates the depth: using the observed (larger) hole-diameters, instead of the laser spot-size, would bring this available-energy vaporization depth closer to quantitative agreement with the data, as would smaller absorption fractions.

From this picture, the 1.2-ps laser-matter interactions appear to drive a vaporization-phase ablation process with the commensurate advantages of ablation carrying the heat away with the evaporated material, leading to little melt-debris and an improved feature-size resolution that is not available with nanosecond or microsecond interactions. A vaporization process was similarly inferred by Zhu et al. for single-pulse femtosecond ablation of aluminum, see X. Zhu, D. M. Villeneuve, A. Y. Naumov, S. Nikumb, P. Corkum, Experimental study of drilling sub-10 micron holes in tin metal foils with femtosecond laser pulses, *Appl. Surf. Sci.* 152, 138–148 (1999).

Summarizing for aluminum, it has been observed that drilling of smooth and relatively clean, high aspect-ratio through-holes in foil thicknesses up to 200 μm with single microsecond bursts provided a faster process than possible with current kHz repetition-rate systems. As a hybrid way of delivering laser-fluence to target, these mode-locked bursts exploit an excellent combination of quasi-cw heating effects to support rapid etching rates and ultrafast-laser interactions for clean ejection of material. Plume-absorption effects are also mitigated to the degree that the 7.5-ns pulse-to-pulse separation supports hydrodynamic expansion of ablation vapor/plasma from the surface. In this way, large aspect-ratio holes could be formed in thick metal foils with a single burst.

Ultrafast laser interactions and thermal diffusion are similar for metals and semiconductors so that the inventors anticipate the general advantages of the present burst-ultrafast processing of aluminum are therefore extensible to this broad and general class of materials. The results of laser machining of glass entails the other extreme of material properties (brittle and high melt/vapour temperatures), demonstrating that burst-ultrafast lasers offer a wide spectrum of applications and advantages in laser processing and laser modification of materials having widely diverse properties.

It will be understood that the method of the present invention may be used for processing in the bulk of the material and is not restricted to processing the surface of the material. In this case the process involves applying laser pulses to a target zone within the body of the material, the laser pulses having a time separation between individual laser pulses sufficiently long to permit acoustic and thermal shock to the material to spread and/or dissipate so that a next subsequent laser pulse is not substantially reflected, scattered and/or absorbed by the temporarily altered material properties. The laser pulses have a time separation between pulses sufficiently short so that, in one embodiment of the invention, a thermal component in the target zone presents heated material to successive ultrafast laser pulses in the burst, control of which residual or accumulated heat serves the purpose of preventing or mitigating against the deleterious effects of material stresses in the material due to acoustic or thermal shock, while optimizing the useful range of such effects.

The method disclosed herein defines a new way of controlling the delivery of laser fluence to optimize performance by utilizing the attributes of ultrafast laser interactions with advantages of long pulse heating or long-pulse modification of the material properties. The heat-induced stresses caused by thermal cycling by known machining approaches, with repetition rates up to multi-kHz, include 'bound' stresses, normally caused by laser-heating. If the material cools down between pulses, stresses are locked into glasses and ceramics. Then the third pulse may cause brittle fracture. The advantages of the present invention include specifically that the high repetition rate avoids thermal cycling (calculate by thermal diffusion times, roughly); also that the low-grade residual heat anneals thermal stresses pre-existing or accumulating in the material. Specific to the present method: picosecond and femtosecond pulses leave only a small residual of heat, suitable to this desired effect, because of the evaporative cooling effect described above. Thus the method disclosed herein of delivering fluence has this special advantage to the material processing not available if the repetition rates are low or if the pulses are not ultrafast.

Thus, in accordance with the present invention, applying high frequency bursts (2, 3, 4, . . . , pulses, through to continuous high repetition rate pulsetrains) at frequencies of 100 kHz to 100's of MHz provides control over the thermal physics and relaxation processes not available with low-pulse (<100 kHz) rate laser systems because thermal transport and relaxation of other properties removes dissipated laser energy not carried away by the plume. The thermal heat and/or modified material extend is intermediate between long pulse interactions and single-ultrafast (<100 kHz) laser interactions. The process is widely applicable to all classes of materials and of general advantage to, but not limited to, the following processes: machining, micromachining, cutting, surface structuring, surface texturing, rapid protyping, annealing, shock treatment, refractive index profiling, laser-induced breakdown spectroscopy, via formation, surface cleaning, pulsed-laser deposition, medical procedures.

The pulse-to-pulse separation (the inverse of repetition rate) is a key control parameter of this novel method that provides several significant advantages. The sufficiently long separation between laser pulses permits hydrodynamic expansion of the plume and/or plasma to avoid laser shielding effects; the subsequent laser pulse is not reflected/absorbed by the plume and all or most of the laser energy strikes the dense target material, for high efficiency energy-coupling. The degree of plume/plasma shielding is controlled by the pulse-to-pulse separation (amongst other parameters such as hole depth or temporal profile of the burst envelope).

Sufficiently short separation retains a thermal component in the target material that presents heated/modified material to successive ultrafast laser pulses in the burst. This thermal component is key to numerous attributes (described below) that are not available with low repetition rate (<100 kHz) ultrafast lasers. The degree of thermal component (surface temperature) is controlled by the pulse-to-pulse duration (amongst other parameters such as fluence, laser spot size). The thermal component can modify permanently the material properties, providing refractive index changes in optical materials, densificiation or swelling of materials, visible marks.

The thermal component can anneal the surrounding material improving the overall quality of the laser process. The annealing process 'heals' a material in certain situations that, for example, eliminates incubation processes that change the absorption and other material properties, and make lower-rep rate laser processing less predictable. Surface swelling can also be avoided and precise rates of processing become available.

The thermal component raises the temperature in the surrounding processing volume, changing the state of the material to one possibly more conducive to the laser process. In brittle materials, the higher temperature confers material ductility, preventing and/or reducing the initiation of microcracks or other defects that can propagate by laser induced shock and other processing mechanisms. This brittle-to-ductile transition is particularly attractive in processing brittle materials such as glasses, wide bandgap materials, semiconductors, ceramics, layered materials, and composites, providing the means for forming excisions without surface cracks, sheared flakes, collateral damage, defect formation and the like.

The thermal component reduces the required laser fluence (per pulse) with several advantages including more energy efficient material removal, excision of high aspect ratio holes, deeper holes are possible and the process is attractive for good conductors such as metals or semiconductors. The burst mode permits the excision of through holes in a single pulse burst in foils and thicker (~1 mm) metal plates, thereby providing faster processing than lower-repetition-rate-applications, as well as low dwell-time advantages.

The present method reduces laser-induced shocking during processing, reducing the potential for damage (microcracking, exfoliation, shearing, delamination) since most laser energy is carried away in plume (ultrafast laser advantage), the small remaining thermal part is controllable by the pulse separation; this avoids gross melting that is characteristic of long pulse (nanosecond or longer) laser processing while retaining the advantages of ultrafast laser processing.

Since ultrafast laser machining frequently supports material vaporization, the high repetition rate (>100 kHz) permits a controlled cooling phase of remaining material that prevents the formation of a melt phase normally present with long pulse or cw laser interactions; this provides better-quality excisions with less debris and splattered melt.

The short pulse-to-pulse duration of the present invention further offers laser interactions with temporarily modified material where complete relaxation of physical and chemical changes brought on by previous pulses have not fully relaxed.

Therefore, the pulse-to-pulse separation is a new control 'knob' to be tuned to an optimal value (typically less than 1000 ns) that depends on parameters including the laser fluence, wavelength, material properties, beam area and layout geometry. The key is to time the pulse separation to optimal conditions such that the surrounding material temperature, phase (shorter increases temperature), physical or chemical properties offer a controlled laser interaction, while permitting enough time for the plume/plasma to expand and open a transparent path to the sample surface for the next pulse. The volume of heated region is controllable, and small, and does not have to damage remaining material thereby minimizing collateral damage. There are, however, circumstances in which this same control could be used to advantage in the opposite way, by controlling pulse-separation times so as to deliberately provide a heated plasma plume which benefits processing, e.g., by excluding or reacting with the ambient atmosphere around the workpiece, by producing a bath of electromagnetic radiation to the workpiece, or by removing adsorbed contaminants on the workpiece surface through plasma bombardment.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

S. Kuper, M Stuke, Femtosecond uv excimer laser ablation, *Appl. Phys. B* 44, 199–204 (1987).
A. C. Tam, J. L. Brand, D. C. Cheng, and W. Zapka, Picosecond laser sputtering of sapphire at 266 nm, *Appl. Phys. Lett.* 55, 2045–2047 (1989).
J. Ihlemann, Excimer Laser ablation of fused silica, *Appl. Surf. Sci.* 54 193–200 (1992).
R. S. Marjoribanks, F. W. Budnik, L. Zhao, G. Kulcsár, M. Stanier, & J. Mihaychuk, High-contrast terawaft chirped-pulse-amplification laser that uses a 1-ps Nd:glass oscillator, *Optics Lett.* 18, 361 (1993).
D. Du, X. Liu, G. Korn, J. Squier, and G. Mourou, Laser-induced breakdown by impact ionization in $SiO_2$ with pulse widths from 7 ns to 150 fs, *Appl. Phys. Lett.* 64, 3071 (1994).
S. Press, M. Stuke, Subpicosecond ultraviolet laser ablation of diamond: nonlinear properties at 248 nm and time-resolved characterization of ablation dynamics, *Appl. Phys. Lett.* 67, 338–340 (1995).
P. P. Pronko, S. K. Dutta, J. Squier, J. V. Rudd, D. Du, G. Mourou, Machining of sub-micron holes using a femtosecond laser at 800 nm, *Optics Comm.* 114, 106–110 (1995).
S. Preuss, A. Demchuk, and M. Stuke, Sub-picosecond UV laser ablation of metals, *Appl. Phys. A*, 61, 33–37 (1995).
C. Momma, B. N. Chichkov, S. Nolte, F. von Alvensleben, A. Tunnermann, H. Welling, B. Wellegehausen, Short-pulse laser ablation of solid targets, Optics Comm., 129, 134–142 (1996).
B. C. Stuart, M. D. Feit, S. Herman, A. M. Rubenchick, B. W. Shore, M. D Perry, Optical ablation by high-power short-pulse lasers, *J. Opt. Soc. Am B* 13, 459–468 (1996).
K. M. Davis, K. Miura, N. Sugimoto, and K. Hirao, Writing waveguides in glass with a femtosecond laser, Opt. Letts. 21, 1729–1731 (1996).
W. Kautek, J. Kruger, M. Lenzner, S. Sartania, C. Spielmann, and F. Krausz, Laser ablation of dielectrics with pulse durations between 20 fs and 3 ps, *Appl. Phys. Lett.* 69, 3146–3148 (1996).
H. Varel, D. Ashkenasi, A. Rosenfeld, R. Herrmann, F. Noack, E. E. B. Campbell, Laser-induced damage in $SiO_2$ and $CaF_2$ with picosecond and femtosecond laser pulses, *Appl. Phys. A* 62, 293–294 (1996).
C. Momma, S. Nolte, B. N. Chichkov, F. von Alvensleben, A. Tunnermann, Precise laser ablation with ultrashort pulses, Appl. Surf. Sci., 109/110, 15–19 (1997).
T. Götz and M. Stuke, Short-pulse UV laser ablation of solid and liquid metals: indium, *Appl. Phys. A*, 64, 539–543 (1997).
X. Liu, D. Du, and G. Mourou, Laser ablation and micromachining with ultrashort laser pulses, *IEEE J. of Quantum Electron.* 33, 1706–1716 (1997).
D. Ashkenasi, H. Varel, A. Rosenfeld, F. Noack, and E. E. B. Campbell, Pulse-width influence on laser structuring of dielectrics, *Nucl. Instr. & Meth. in Phys. Res. B* 122, 359–363 (1997).
H. Varel, D. Ashkenasi, A. Rosenfeld, M. Whamer, E. E. B. Campbell, Micromachining of quartz with ultrashort laser pulses, *Appl. Phys. A* 65, 367–373 (1997).
D. von der Linde, K. Sokolowski-Tinten, and J. Bialkowski, Laser-solid interaction in the femtosecond time regime, *Appl. Surf. Sci.* 109/110, 1–10 (1997).
C. B. Schaffer, A. Brodeur, N. Nishimura, and E. Mazur, Laser-induced microexplosions in transparent materials: microstructuring with nanojoules, *SPIE* 3616, 143 (1999).
J.-X. Zhao, B. Hüttner, and A. Menschig, Micromachining with ultrashort laser pulses, SPIE Proc Vol. 3618, 114–121 (1999).
X. Zhu, D. M. Villeneuve, A. Y. Naumov, S. Nikumb, P. Corkum, Experimental study of drilling sub-10 micron holes in tin metal foils with femtosecond laser pulses, *Appl. Surf. Sci.* 152, 138–148 (1999).

Therefore what is claimed is:

1. A method of laser induced modification of a material, comprising:
applying at least one burst of laser pulses to a material, the laser pulses having a time separation between individual laser pulses in a range appropriate so as to exploit the persistence of a selected transient effect arising from the interaction of a previous pulse with the material, said laser pulses having a pulse width of less than about 10 picoseconds, and collectively having fluence above a threshold value for modification of said material.

2. The method according to claim 1, wherein the time separation between individual laser pulses is less than a maximum time determined by a characteristic relaxation time of said transient effect.

3. The method according to claim 2, wherein said transient effect is thermal transport and said maximum time separation between individual pulses is about 10 microseconds, this value being determined by material characteristics and interaction geometry between said laser pulses and said material.

4. The method according to claim 3 wherein said at least one burst of laser pulses includes a preselected number of laser pulses greater than or equal to two.

5. The method according to claim 3 including detecting electromagnetic radiation emitted from a portion of said material at which said laser pulses are applied for spectroscopic analysis.

6. The method according to claim 3 including coating a substrate placed in close proximity to said material, wherein said substrate is coated by spallation or evaporation of matter ejected from said material.

7. The method according to claim 3 wherein said material is glass and said modification is drilling holes therein, cutting or machining a surface of said glass, and wherein said pulse widths are less than about 10 picoseconds and pulse-separation times are less than 10 about microseconds.

8. The method according to claim 3 wherein said material is a dielectric and said modification is drilling holes therein, cutting or machining a surface of said dielectrics, and wherein said pulse widths are less than about 10 picoseconds and pulse-separation times are less than 10 about microseconds.

9. The method according to claim 3 wherein said material is a semiconductor and said modification is drilling holes therein, cutting or machining a surface of said semiconductor, and wherein said pulse widths are less than about 10 picoseconds and pulse-separation times are less than 10 about microseconds.

10. The method according to claim 3 wherein said material is metal and said modification is drilling holes therein, cutting or machining a surface of said metal, and wherein said pulse widths are less than about 10 picoseconds and pulse-separation times are less than about 10 microseconds.

11. The method according to claim 10 wherein said metal is aluminum.

12. The method according to claim 3 wherein said material is a ceramic and said modification is drilling holes therein, cutting or machining a surface of said ceramic, and wherein said pulse widths are less than about 10 picoseconds and pulse-separation times are less than about 10 microseconds.

13. The method according to claim 3 wherein said material is glass and said modification is altering an index of refraction at a surface or within a bulk of the glass, and wherein said pulse widths are less than about 1 picosecond and pulse-separation times are less than about 10 microseconds.

14. The method according to claim 3 wherein said material is glass and said modification is mechanical modification including compactification, inducing stress/strain features, relief of stress/strain features, or optical damage.

15. The method according to claim 3 wherein said material is substantially transparent biological tissue and said modification is photorefractive surgery, or diffractive correction, by tissue ablation.

16. The method according to claim 3 wherein said material is substantially transparent biological tissue and said modification is photorefractive surgery, or diffractive correction, by tissue modification, including protein denaturation.

17. The method according to claim 3 wherein said material is protein and wherein said modification is protein denaturation.

18. The method according to claim 3 wherein an amplitude of the pulsetrain is shaped or controlled so that individual pulses have intensities different from other pulses in the pulsetrain and tailored to a specific material or processing application.

19. The method according to claim 18 wherein a spatial intensity of the laser pulsetrain burst is determined by optical imagining, including patterning by optical amplitude-masks or by diffractive optical elements.

* * * * *